(12) United States Patent
Hida et al.

(10) Patent No.: US 9,644,148 B2
(45) Date of Patent: May 9, 2017

(54) LIQUID CRYSTAL COMPOSITION

(71) Applicant: SUMITOMO CHEMICAL COMPANY, LIMITED, Tokyo (JP)

(72) Inventors: Noriyuki Hida, Osaka (JP); Haruki Okawa, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/719,854

(22) Filed: May 22, 2015

(65) Prior Publication Data

US 2015/0337203 A1 Nov. 26, 2015

(30) Foreign Application Priority Data

May 26, 2014 (JP) .................. 2014-107846

(51) Int. Cl.
*C07C 211/54* (2006.01)
*C09K 19/60* (2006.01)
(Continued)

(52) U.S. Cl.
CPC .......... *C09K 19/601* (2013.01); *C07C 245/08* (2013.01); *C07D 295/04* (2013.01);
(Continued)

(58) Field of Classification Search
CPC .................................................. C09K 19/601
See application file for complete search history.

(56) References Cited

U.S. PATENT DOCUMENTS 7,763,330 B2 7/2010 Lub et al.
8,383,212 B2 2/2013 Obata et al.

FOREIGN PATENT DOCUMENTS

JP 56-104984 8/1981
JP S58-38756 A 3/1983
(Continued)

OTHER PUBLICATIONS

T. Kozlecki, et al., "4-Lithio-4'-alkylazobenzenes as Convenient Intermediates for the Preparation of Azobenzene Derivatives", Synthesis, Jun. 1997, vol. 6, pp. 681-684.
(Continued)

*Primary Examiner* — Chanceity Robinson
(74) *Attorney, Agent, or Firm* — Sughrue Mion, PLLC

(57) ABSTRACT

Provided is a composition that can form a polarizing film with high dichroic ratio, which contains a compound having a function as a dichroic dye and having a local maximum absorption in a wavelength range of 350 to 550 nm. The composition contains a compound represented by the formula (1) and a polymerizable liquid crystal compound:

$$R^1-\underset{(R^7)_p}{\underline{\phantom{XXX}}}-N=N-Y-\underset{(R^8)_q}{\underline{\phantom{XXX}}}-N\underset{R^3}{\overset{R^2}{\diagup}} \quad (1)$$

wherein Y represents a group represented by the formula (Y1) or the formula (Y2)

$$*-\underset{\phantom{X}}{\underline{\phantom{XXX}}}- \quad (Y1)$$

(Continued)

-continued

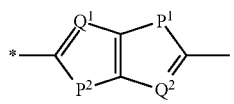
(Y2)

14 Claims, 3 Drawing Sheets

(51) Int. Cl.
C07C 245/08 (2006.01)
H01L 51/00 (2006.01)
G02F 1/1335 (2006.01)
H01L 51/52 (2006.01)
C09K 19/20 (2006.01)
G02B 5/30 (2006.01)
C07D 513/04 (2006.01)
C07D 295/135 (2006.01)
C09D 7/12 (2006.01)
C07D 495/04 (2006.01)
C07D 295/04 (2006.01)
C09D 4/00 (2006.01)
C08F 220/18 (2006.01)

(52) U.S. Cl.
CPC ....... *C07D 295/135* (2013.01); *C07D 495/04* (2013.01); *C07D 513/04* (2013.01); *C09D 7/12* (2013.01); *C09K 19/2007* (2013.01); *G02B 5/30* (2013.01); *G02B 5/305* (2013.01); *G02B 5/3083* (2013.01); *G02F 1/133514* (2013.01); *G02F 1/133528* (2013.01); *H01L 51/005* (2013.01); *H01L 51/0035* (2013.01); *H01L 51/5281* (2013.01); *C08F 220/18* (2013.01); *C09D 4/00* (2013.01); *C09K 2019/2035* (2013.01)

(56) References Cited

FOREIGN PATENT DOCUMENTS

| JP | 06-034976 A | 2/1994 |
| JP | 2007-510946 A | 4/2007 |
| JP | 4719156 B2 | 4/2011 |
| JP | 2011-242743 A | 12/2011 |

OTHER PUBLICATIONS

W.H. Nutting, et al., "4-(4-Nitrophenylazo)benzoic Acid, Improved Synthesis of Its Acid Chloride and Spectroscopic Properties of Its Esters", The Journal of Organic Chemistry, Feb. 1970, vol. 35, No. 2, pp. 505-506.

Alexander Rossler and Peter Boldt, "Improved access to thiazolo[5,4-(d]thiazole and thieno[2,3-d]thiazole", Journal of Chemical Society, Perkin Trans. 1, 1998, pp. 685-686.

Tatsuo Ishiyama, et al., "Palladium(0)-Catalyzed Cross-Coupling Reaction of Alkoxydiboron with Haloarenes: A Direct Procedure for Arylboronic Esters", Journal of Organic Chemistry, 1995, vol. 60, pp. 7508-7510.

Norio Miyaura and Akira Suzuki, "Palladium-Catalyzed Cross-Coupling Reactions of Organoboron Compounds", Chemical Reviews, 1995, vol. 95, No. 7, pp. 2457-2483.

J. Lub, et al., "The synthesis of liquid-crystalline diacrylates derived from cyclohexane units", Recueil des Travaux Chimiques des Pays-Bas, 1996, vol. 115, pp. 321-328.

LIQUID CRYSTAL COMPOSITION

BACKGROUND OF THE INVENTION

Field of the Invention

The present invention relates to a composition.

Description of the Related Art

JP 2007-510946 W describes a polarizing film containing a dichroic light-absorbing compound (dichroic dye) dispersed in an oriented polymerizable liquid crystal compound.

Japanese Patent 1454637 (JP 63-1357 B) describes a bisazo type dye having 1,4-naphthyl structure as a dichroic dye having a local maximum absorption in a wavelength range of 390 to 550 nm. However, a polarizing film having the dichroic dye has a low dichroic ratio.

A composition has been demanded which has a local maximum absorption in a wavelength range of 350 to 550 nm, contains a compound having a function as a dichroic dye, and can form a polarizing film with high dichroic ratio.

A composition has been demanded that can form a polarizing film with high dichroic ratio, which contains a compound having a function as a dichroic dye and having a local maximum absorption in a wavelength range of 350 to 550 nm.

SUMMARY OF THE INVENTION

The present invention includes the following aspects.

[1] A composition comprising a compound represented by the formula (1) and a polymerizable liquid crystal compound:

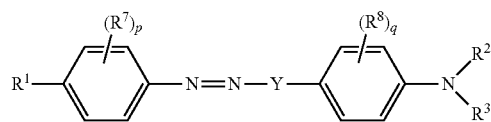

(1)

wherein Y represents a group represented by the formula (Y1) or the formula (Y2);

$R^1$ represents an alkyl group having 1 to 20 carbon atoms, an alkoxy group having 1 to 20 carbon atoms, or —N(R)($R^0$); wherein R and $R^0$ each independently represent a hydrogen atom or an alkyl group having 1 to 10 carbon atoms, or R and $R^0$ are bonded together to form a ring together with the nitrogen atom to which R and $R^0$ are bonded; one or more hydrogen atoms constituting the alkyl group having 1 to 20 carbon atoms, the alkoxy group having 1 to 20 carbon atoms, or the alkyl group having 1 to 10 carbon atoms are independently optionally substituted with an atom or a group selected from the group consisting of a halogen atom, a hydroxyl group and an optionally substituted amino group; the alkyl group having 1 to 20 carbon atoms, the alkoxy group having 1 to 20 carbon atoms, and the alkyl group having 1 to 10 carbon atoms each optionally have an ether linkage (—O—) between carbon atoms constituting them;

$R^7$ and $R^8$ are substituents other than a hydrogen atom and are each independently an alkyl group having 1 to 4 carbon atoms, an alkoxy group having 1 to 4 carbon atoms, a halogen atom, or a cyano group; one or more hydrogen atoms constituting the alkyl group having 1 to 4 carbon atoms or the alkoxy group having 1 to 4 carbon atoms are independently optionally substituted with a halogen atom or a hydroxyl group; p and q are each independently an integer of 0 to 2;

$R^2$ and $R^3$ each independently represent a hydrogen atom or an alkyl group having 1 to 10 carbon atoms, or $R^2$ and $R^3$ are bonded together to form a ring together with the nitrogen atom to which $R^2$ and $R^3$ are bonded; one or more hydrogen atoms constituting the alkyl group having 1 to 10 carbon atoms are independently optionally substituted with an atom or a group selected from the group consisting of a halogen atom, a hydroxyl group and an optionally substituted amino group; and the alkyl group having 1 to 10 carbon atoms optionally have an ether linkage (—O—) between carbon atoms constituting it;

(Y1)

(Y2)

wherein * shows a bonding site to N;

$P^1$ and $P^2$ each independently represent a sulfur atom, an oxygen atom or —$NR^{10}$— wherein $R^{10}$ represents a hydrogen atom or an alkyl group having 1 to 4 carbon atoms;

$Q^1$ and $Q^2$ each independently represent a nitrogen atom or =CH—.

[2] The composition according to [1], wherein the compound represented by the formula (1) is a compound represented by the formula (1a):

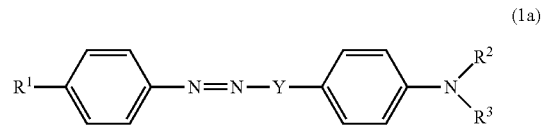

(1a)

wherein Y and $R^1$ to $R^3$ respectively represent as defined in [1].

[3] The composition according to [1] or [2], wherein the polymerizable liquid crystal compound exhibits a smectic liquid crystal phase.

[4] The composition according to any one of [1] to [3], wherein the compound further comprises a polymerization initiator.

[5] A polarizing film formed from the composition according to any one of [1] to [4].

[6] The polarizing film according to [5], wherein a local maximum absorption wavelength (λmax1) of the polarizing film according to [5] is longer than a local maximum absorption wavelength (λmax2) of the compound represented by the formula (1) contained in the polarizing film.

[7] The polarizing film according to [6], wherein a difference between λmax 1 and λmax 2 is 15 nm or longer.

[8] The polarizing film according to any one of [5] to [7], wherein the polarizing film exhibits a Bragg peak in x-diffraction measurement.

[9] A liquid crystal display device comprising the polarizing film according to any one of [5] to [8].

[10] A liquid crystal cell comprising a substrate, a liquid crystal layer, and the polarizing film according to any one of [5] to [8].
[11] The liquid crystal cell according to [10], wherein the polarizing film is disposed between the substrate and the liquid crystal layer.
[12] The liquid crystal cell according to [11], further comprising a color filter disposed between the substrate and the liquid crystal layer.
[13] A circularly polarizing plate comprising the polarizing film according to any one of [5] to [8] and a ¼ wavelength plate.
[14] An organic EL display device comprising the circularly polarizing plate according to [13] and an organic EL element.
[15] A method for producing a compound represented by the formula (1), comprising reacting of a compound represented by the formula (2) with a compound represented by the formula (3):

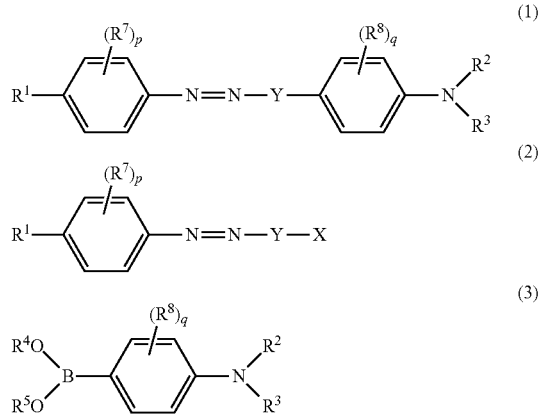

wherein Y is a group represented by the formula (Y1) or the formula (Y2);

$R^1$ is an alkyl group having 1 to 20 carbon atoms, an alkoxy group having 1 to 20 carbon atoms, or —N(R)(R$^0$); R and R$^0$ are each independently a hydrogen atom or an alkyl group having 1 to 10 carbon atoms, or R and R$^0$ are bonded together to form a ring together with the nitrogen atom to which R and R$^0$ are bonded; one or more hydrogen atoms constituting the alkyl group having 1 to 20 carbon atoms, the alkoxy group having 1 to 20 carbon atoms, or the alkyl group having 1 to 10 carbon atoms are independently optionally substituted with an atom or a group selected from the group consisting of a halogen atom, a hydroxyl group and an amino group which are optionally substituted; the alkyl group having 1 to 20 carbon atoms, the alkoxy group having 1 to 20 carbon atoms, and the alkyl group having 1 to 10 carbon atoms each optionally have an ether linkage (—O—) between carbon atoms constituting them;

$R^7$ and $R^8$ are substituents other than a hydrogen atom and are each independently an alkyl group having 1 to 4 carbon atoms, an alkoxy group having 1 to 4 carbon atoms, a halogen atom, or a cyano group; one or more hydrogen atoms constituting the alkyl group having 1 to 4 carbon atoms or the alkoxy group having 1 to 4 carbon atoms is independently optionally substituted with a halogen atom or a hydroxyl group; p and q are each independently an integer of 0 to 2;

$R^2$ and $R^3$ are each independently a hydrogen atom or an alkyl group having 1 to 10 carbon atoms, or $R^2$ and $R^3$ are bonded together to form a ring together with the nitrogen atom to which $R^2$ and $R^3$ are bonded; one or more hydrogen atoms constituting the alkyl group having 1 to 10 carbon atoms are independently optionally substituted with an atom or a group selected from the group consisting of a halogen atom, a hydroxyl group or an amino group which is optionally substituted; and the alkyl group having 1 to 10 carbon atoms each optionally have an ether linkage (—O—) between carbon atoms constituting them;

X is a chlorine atom, a bromine atom or an iodine atom;
$R^4$ and $R^5$ are each independently a hydrogen atom or an alkyl group having 1 to 10 carbon atoms, or $R^4$ and $R^5$ are bonded together to form a ring together with the oxygen atom and the boron atom to which $R^4$ and $R^5$ are bonded;

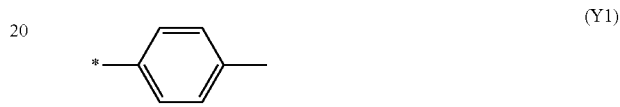

wherein * shows a bonding site to N;
$P^1$ and $P^2$ each independently represent a sulfur atom, an oxygen atom or —NR$^{10}$— wherein $R^{10}$ is a hydrogen atom or an alkyl group having 1 to 4 carbon atoms;
$Q^1$ and $Q^2$ each independently represent a nitrogen atom or =CH—.

[16] A compound represented by the formula (5):

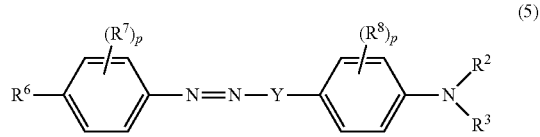

wherein Y is a group represented by the formula (Y1) or the formula (Y2);

$R^6$ is an alkyl group having 2 to 20 carbon atoms, an alkoxy group having 1 to 20 carbon atoms, or —N(R)(R$^0$); R and R$^0$ are each independently a hydrogen atom or an alkyl group having 1 to 10 carbon atoms, or R and R$^0$ are bonded together to form a ring together with the nitrogen atom to which R and R$^0$ are bonded; one or more hydrogen atoms constituting the alkyl group having 2 to 20 carbon atoms, the alkoxy group having 1 to 20 carbon atoms, or the alkyl group having 1 to 10 carbon atoms are independently optionally substituted with an atom or a group selected from the group consisting of a halogen atom, a hydroxyl group and an amino group which are optionally substituted; the alkyl group having 2 to 20 carbon atoms, the alkoxy group having 1 to 20 carbon atoms, and the alkyl group having 1 to 10 carbon atoms each optionally have an ether linkage (—O—) between carbon atoms constituting them;

$R^7$ and $R^8$ are substituents other than a hydrogen atom and are each independently an alkyl group having 1 to 4 carbon atoms, an alkoxy group having 1 to 4 carbon atoms, a halogen atom, or a cyano group; one or more hydrogen atoms constituting the alkyl group having 1 to 4 carbon atoms or the alkoxy group having 1 to 4 carbon atoms are independently optionally substituted with a halogen atom or a hydroxyl group; p and q are each independently an integer of 0 to 2;

R² and R³ are each independently a hydrogen atom or an alkyl group having 1 to 10 carbon atoms, or R² and R³ are bonded together to form a ring together with the nitrogen atom to which R² and R³ are bonded; one or more hydrogen atoms constituting the alkyl group having 1 to 10 carbon atoms are independently optionally substituted with an atom or a group selected from the group consisting of a halogen atom, a hydroxyl group and an amino group which are optionally substituted; and the alkyl group having 1 to 10 carbon atoms each optionally have an ether linkage (—O—) between carbon atoms constituting them;

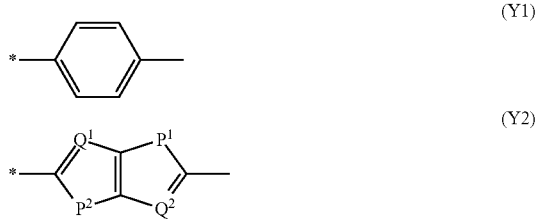

wherein * shows a bonding site to N;
P¹ and P² each independently represent a sulfur atom, an oxygen atom or —NR¹⁰— wherein R¹⁰ is a hydrogen atom or an alkyl group having 1 to 4 carbon atoms;
Q¹ and Q² are each independently a nitrogen atom or =CH—.

[17] The compound according to [16], wherein the compound represented by the formula (5) is represented by the formula (5a):

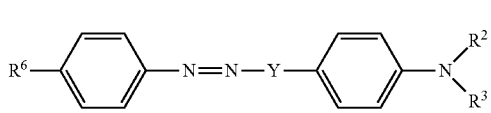

wherein Y, R², R³, and R⁶ respectively represent as defined in [15].

[18] A polarizing film comprising the compound according to [16] or [17].

[19] A liquid crystal display device comprising the polarizing film according to [18].

[20] A liquid crystal cell comprising a substrate, a liquid crystal layer, and the polarizing film according to [18].

[21] An organic EL display device comprising the polarizing film according to [18].

The composition of the present invention contains a compound which has a local maximum absorption in a wavelength range of 390 to 550 nm and has a function as a dichroic dye. According to the composition, a polarizing film with a high dichroic ratio can be formed.

DETAILED DESCRIPTION OF THE PREFERRED EMBODIMENTS

Figure 1:
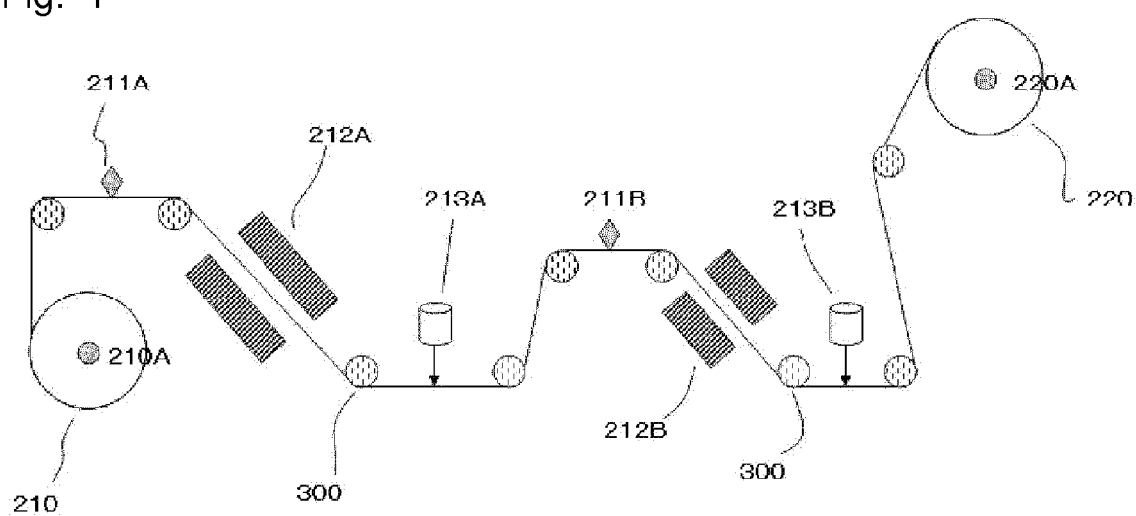
FIG. 1 is a schematic diagram illustrating a continuous production method for the polarizing film of the present invention.

The composition of the present invention contains a compound represented by the formula (1) (hereinafter, may be sometimes referred to as compound (1)) and a polymerizable liquid crystal compound.

<Compound (1)>

The azo group of the compound (1) is preferable to be a trans-form.

In the formula (Y1) and the formula (Y2), P¹ and P² are preferably sulfur atoms.

The alkyl group having 1 to 4 carbon atoms represented by R¹⁰ may be a methyl group, an ethyl group, a n-propyl group, an isopropyl group, a n-butyl group, an isobutyl group, a tert-butyl group, or the like.

Either one of Q¹ and Q² is preferably a nitrogen atom. Q¹ is more preferably =CH—. Q² is more preferably a nitrogen atom.

In the formula (1), R¹ represents an alkyl group having 1 to 20 carbon atoms, an alkoxy group having 1 to 20 carbon atoms, or a group represented by —N(R)(R⁰). R¹ is preferably an alkyl group having 1 to 20 carbon atoms or a group represented by —N(R)(R⁰).

The alkyl group having 1 to 20 carbon atoms represented by R¹ may be a linear or branched alkyl group such as methyl group, ethyl group, n-propyl group, isopropyl group, n-butyl group, isobutyl group, tert-butyl group, n-pentyl group, isopentyl group, neopentyl group, n-hexyl group, n-heptyl group, n-octyl group, n-nonyl group, or n-decyl group.

One or more hydrogen atoms constituting the alkyl group having 1 to 20 carbon atoms are independently optionally substituted with a halogen atom such as fluorine atom, hydroxyl group, or optionally substituted amino group. Examples of the optionally substituted amino group may include an amino group in which one or two hydrogen atoms are substituted with an alkyl group having 1 to 20 carbon atoms such as N-methylamino group, N-ethylamino group, N,N-dimethylamino group, or N,N-diethylamino group. Examples thereof may include haloalkyl groups having 1 to 20 carbon atoms such as fluoromethyl group, trifluoromethyl group, pentafluoroethyl group and nonafluorobutyl group; hydroxyalkyl groups having 1 to 20 carbon atoms such as hydroxymethyl group and 2-hydroxyethyl group; and alkyl groups having 1 to 20 carbon atoms and having an optionally substituted amino group such as aminomethyl group and 2-(N,N-dimethylamino)ethyl group.

The alkyl group having 1 to 20 carbon atoms represented by R¹ each optionally have an ether linkage (—O—) between carbon atoms constituting them. The alkyl group having an ether linkage between carbon atoms may be a methoxymethyl group, a 2-ethoxyethyl group, a 2-(2-ethoxyethoxy)ethyl group, a 2-[2-(ethylamino)ethylamino]ethoxy group, etc. The alkyl group having 1 to 20 carbon atoms represented by R¹ is preferably an unsubstituted linear or branched alkyl group.

The alkoxy group having 1 to 20 carbon atoms represented by $R^1$ may be an unsubstituted linear or branched alkoxy group such as methoxy group, ethoxy group, n-propoxy group, isopropoxy group, n-butoxy group, isobutoxy group, tert-butoxy group, n-pentyloxy group, isopentyloxy group, neopentyloxy group, n-hexyloxy group, n-heptyloxy group, n-octyloxy group, n-nonyloxy group, n-decyloxy group, etc.

One or more hydrogen atoms constituting the alkoxy group having 1 to 20 carbon atoms are independently optionally substituted with a halogen atom such as fluorine atom, hydroxyl group, or optionally substituted amino group. Examples of the optionally substituted amino group may include an amino group in which one or two hydrogen atoms are substituted with an alkyl group having 1 to 20 carbon atoms such as N-methylamino group, N-ethylamino group, N,N-dimethyl amino group, or N,N-diethylamino group. Examples thereof may include haloalkoxy groups having 1 to 20 carbon atoms such as fluoromethoxy group, trifluoromethoxy group, pentafluoroethoxy group and nonafluorobutoxy group; hydroxyalkoxy groups having 1 to 20 carbon atoms such as hydroxymethoxy group and 2-hydroxyethoxy group; and alkoxy groups having 1 to 20 carbon atoms and having an optionally substituted amino group such as aminomethoxy group and 2-(N,N-dimethylamino)ethoxy group.

The alkoxy group having 1 to 20 carbon atoms represented by $R^1$ each optionally has an ether linkage (—O—) between carbon atoms constituting them. The alkoxy having an ether linkage between carbon atoms may be a methoxymethoxy group, a 2-ethoxyethoxy group, a 2-(2-ethoxyethyl)ethoxy group, a 2-[2-(ethylamino)ethylamino]ethoxy group, etc. The alkoxy group having 1 to 20 carbon atoms represented by $R^1$ is preferably an unsubstituted linear or branched alkoxy group.

When the $R^1$ is —N(R)($R^0$), R and $R^0$ each independently represent a hydrogen atom or an alkyl group having 1 to 10 carbon atoms, or R and $R^0$ are bonded together to form a ring together with the nitrogen atom to which R and $R^0$ are bonded.

The alkyl group having 1 to 10 carbon atoms represented by R may be a linear or branched alkyl group such as methyl group, ethyl group, n-propyl group, isopropyl group, n-butyl group, isobutyl group, tert-butyl group, n-pentyl group, isopentyl group, neopentyl group, n-hexyl group, n-heptyl group, n-octyl group, n-nonyl group, n-decyl group, etc.

One or more hydrogen atoms constituting the alkoxy group having 1 to 10 carbon atoms are independently optionally substituted with a halogen atom such as fluorine atom, hydroxyl group, or optionally substituted amino group. Examples of the optionally substituted amino group may include an amino group in which one or two hydrogen atoms are substituted with an alkyl group having 1 to 10 carbon atoms such as N-methylamino group, N-ethylamino group, N,N-dimethyl amino group, or N,N-diethylamino group. Examples thereof may include haloalkyl groups having 1 to 10 carbon atoms such as fluoromethyl group, trifluoromethyl group, pentafluoroethyl group and nonafluorobutyl group; hydroxyalkyl groups having 1 to 10 carbon atoms such as hydroxymethyl group and 2-hydroxyethyl group; and alkyl groups having 1 to 10 carbon atoms and having an optionally substituted amino group such as aminomethyl group and 2-(N,N-dimethylamino)ethyl group.

The alkyl group having 1 to 10 carbon atoms represented by R each optionally has an ether linkage (—O—) between carbon atoms constituting them. The alkyl group having an ether linkage between carbon atoms may be a methoxymethyl group, a 2-ethoxyethyl group, a 2-(2-ethoxyethoxy)ethyl group, a 2-[2-(ethylamino)ethylamino]ethoxy group, etc. The alkyl group having 1 to 10 carbon atoms represented by R is preferably an unsubstituted linear or branched alkyl group.

The alkyl group having 1 to 10 carbon atoms represented by $R^0$ may be the same as those described as examples of the alkyl group having 1 to 10 carbon atoms represented by R. The alkyl group having 1 to 10 carbon atoms represented by $R^0$ is preferably an unsubstituted linear or branched alkyl group.

—N(R)($R^0$) may be an amino group, a methylamino group, a dimethylamino group, an ethylamino group, a diethylamino group, a pyrrolidinyl group, a piperidinyl group, a morpholino group, a thiomorpholino group, a 3,5-dimethylmorpholino group, a 3-ethylthiomorpholino group, etc.

When R and $R^0$ are bonded together to form a ring together with the nitrogen atom to which R and $R^0$ are bonded, the ring to be formed may be a 4- to 10-member ring and may be a heterocyclic ring. The heterocyclic ring refers to an alicyclic hydrocarbon ring, having 4 to 10 carbon atoms, in which one or more methylene groups are substituted with an imino group (—NH—) or a heteroatom such as oxygen atom or sulfur atom. The ring to be formed is preferably a 5- to 7-membered ring.

In each of two phenylene groups of the formula (1), one or more hydrogen atoms constituting these phenylene groups are optionally substituted with a substituent $R^7$ or $R^8$ other than hydrogen. $R^7$ and $R^8$ each independently represent an alkyl group having 1 to 4 carbon atoms, an alkoxy group having 1 to 4 carbon atoms, a halogen atom, or a cyano group. $R^7$ and $R^8$ are each independently optionally substituted with a hydrogen atom at any position of the phenylene groups.

The alkyl group having 1 to 4 carbon atoms may be an unsubstituted linear or branched alkyl group such as methyl group, ethyl group, n-propyl group, isopropyl group, n-butyl group, isobutyl group or tert-butyl group.

One or more hydrogen atoms constituting the alkyl group having 1 to 4 carbon atoms are independently optionally substituted with a halogen atom such as fluorine atom or hydroxyl group. Examples thereof may include haloalkyl groups having 1 to 4 carbon atoms such as fluoromethyl group, trifluoromethyl group, pentafluoroethyl group and nonafluorobutyl group; and hydroxyalkyl groups having 1 to 4 carbon atoms such as hydroxymethyl group and 2-hydroxyethyl group.

The alkoxy group having 1 to 4 carbon atoms may be an unsubstituted linear or branched alkoxy group such as methoxy group, ethoxy group, n-propoxy group, isopropoxy group, n-butoxy group, isobutoxy group or tert-butoxy group.

One or more hydrogen atoms constituting the alkoxy group having 1 to 4 carbon atoms are independently optionally substituted with a halogen atom such as fluorine atom or hydroxyl group. Examples thereof may include haloalkoxy groups having 1 to 4 carbon atoms such as fluoromethoxy group, trifluoromethoxy group, pentafluoroethoxy group and nonafluorobutyl group; and hydroxyalkoxy groups having 1 to 4 carbon atoms such as hydroxymethoxy group and 2-hydroxyethoxy group.

In the formula (1), $R^2$ and $R^3$ each independently represent a hydrogen atom or an alkyl group having 1 to 10 carbon atoms, or $R^2$ and $R^3$ are bonded together to form a ring together with the nitrogen atom to which $R^2$ and $R^3$ are bonded. The alkyl group having 1 to 10 carbon atoms represented by $R^2$ and the alkyl group having 1 to 10 carbon atoms represented by $R^3$ may be the same as those described as examples of the alkyl group having 1 to 10 carbon atoms represented by R. The alkyl group having 1 to 10 carbon atoms represented by $R^2$ and $R^3$ is preferably an unsubstituted linear or branched alkyl group.

—$N(R^2)(R^3)$ may be an amino group, a methylamino group, a dimethylamino group, an ethylamino group, a diethylamino group, a pyrrolidinyl group, a piperidinyl group, a morpholino group, a thiomorpholino group, a 3,5-dimethylmorpholino group, a 3-ethylthiomorpholino group, etc.

When $R^2$ and $R^3$ are bonded together to form a ring together with the nitrogen atom to which $R^2$ and $R^3$ are bonded, the ring to be formed may be the same as those described as examples of the —$N(R)(R^0)$.

In the formula (1), p and q each independently represent an integer of 0 to 2, and more preferably both 0. In this case, the compound (1) becomes a compound represented by the formula (1a):

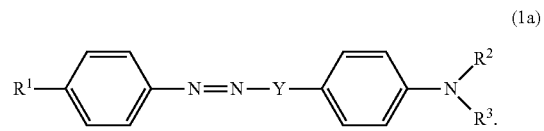
(1a)

The preferable compound (1) may specifically be compounds represented by the formula (1-1) to the formula (1-39).

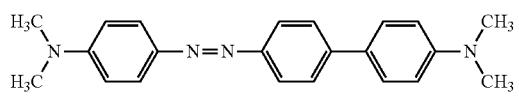
(1-1)

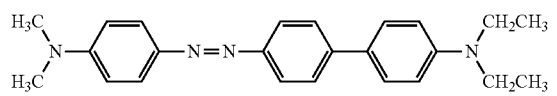
(1-2)

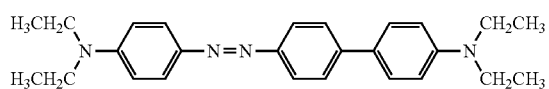
(1-3)

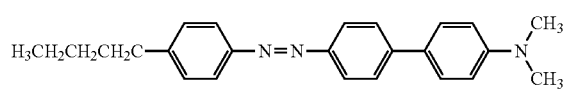
(1-4)

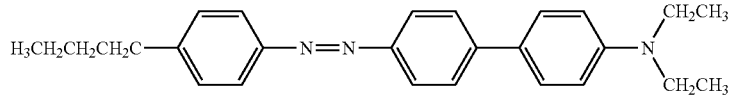
(1-5)

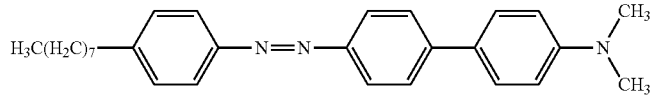
(1-6)

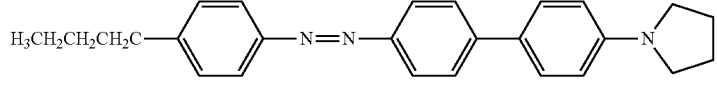
(1-7)

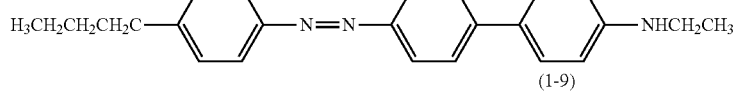
(1-8)

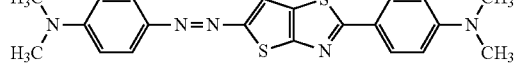
(1-9)

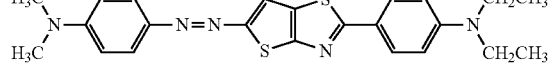
(1-10)

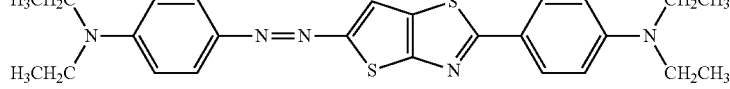
(1-11)

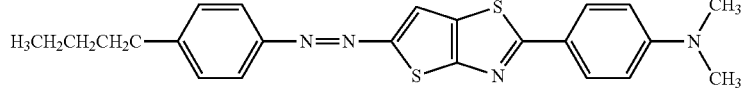
(1-12)

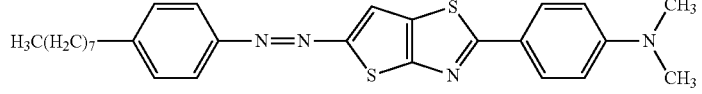
(1-13)

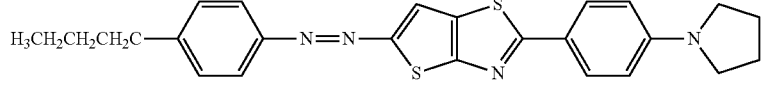
(1-14)

-continued (1-15)

(1-16) (1-17)

(1-18) (1-19)

(1-20) (1-21)

(1-22) (1-23)

(1-24) (1-25)

(1-26) (1-27)

(1-28) (1-29)

(1-30)

(1-31)

(1-32)

(1-33)

(1-34) (1-35)

(1-36) (1-37)

(1-38)

(1-39)

[Structure: CF3-phenyl-N=N-thienothiazole-phenyl-NH-CH2CH2-N(CH3)-]

Especially, compounds represented by the formula (1-3), the formula (1-4), the formula (1-5), the formula (1-12) and the formula (1-13) are more preferable, and compounds represented by the formula (1-4) or the formula (1-13) are furthermore preferable.

The present composition may contain one or more kinds of the compound (1).

The compound (1) is obtained by reaction of a compound represented by the formula (2) (hereinafter, may be sometimes referred to as compound (2)) and a compound represented by the formula (3) (hereinafter, may be sometimes referred to as compound (3)):

$$R^1-\text{Ar}(R^7)_p-N=N-Y-X \quad (2)$$

$$R^4O,R^5O-B-\text{Ar}(R^8)_q-N(R^2)(R^3) \quad (3)$$

X in the compound (2) is preferably a bromine atom.

An alkyl group having 1 to 10 carbon atoms represented by $R^4$ and an alkyl group having 1 to 10 carbon atoms represented by $R^5$ in the compound (3) may be each a linear or branched alkyl group such as methyl group, ethyl group, n-propyl group, isopropyl group, n-butyl group, isobutyl group, tert-butyl group, n-pentyl group, isopentyl group, neopentyl group, n-hexyl group, n-heptyl group, n-octyl group, n-nonyl group or n-decyl group.

—B(OR$^4$)(OR$^5$) may be boronic acid, boronic acid dimethyl group ester, boronic acid diethyl ester, boronic acid pinacol ester, etc., and preferably boronic acid.

In the formulas (2) and (3), $R^1$, $R^2$, $R^3$, $R^7$, $R^8$, p and q are the same as those described in the formula (1).

The preferable compound (2) may specifically be compounds represented by the formula (2-1) to the formula (2-25). The compound (2) may be a commercialized compound, or may be synthesized according to the method described in Synthesis, 1997, 6, 681, Journal of Organic Chemistry, 1970, 35, 505, or may be synthesized from a precursor amino group-isomer obtained according to the method disclosed in JP 58-38756 A by Sandmeyer reaction. The Sandmeyer reaction can be carried out according to the method described in Journal of Chemical Society, Perkin Trans. 1998, 685.

(2-1) (CH3)2N-C6H4-N=N-C6H4-Br (2-2) (CH3)2N-C6H4-N=N-C6H4-I (2-3) (CH3CH2)2N-C6H4-N=N-C6H4-Br (2-4) H3CH2CH2CH2C-C6H4-N=N-C6H4-Cl (2-5) H3CH2CH2CH2C-C6H4-N=N-C6H4-Br (2-6) H3CH2CH2CH2C-C6H4-N=N-C6H4-I (2-7) H3C(H2C)7-C6H4-N=N-C6H4-Br (2-8) H3C(H2C)7-C6H4-N=N-C6H4-I (2-9) (CH3)2N-C6H4-N=N-thienothiazole-Br (2-10) (CH3)2N-C6H4-N=N-thienothiazole-I (2-11) (CH3CH2)2N-C6H4-N=N-thienothiazole-Br (2-12) H3CH2CH2CH2C-C6H4-N=N-thienothiazole-Cl

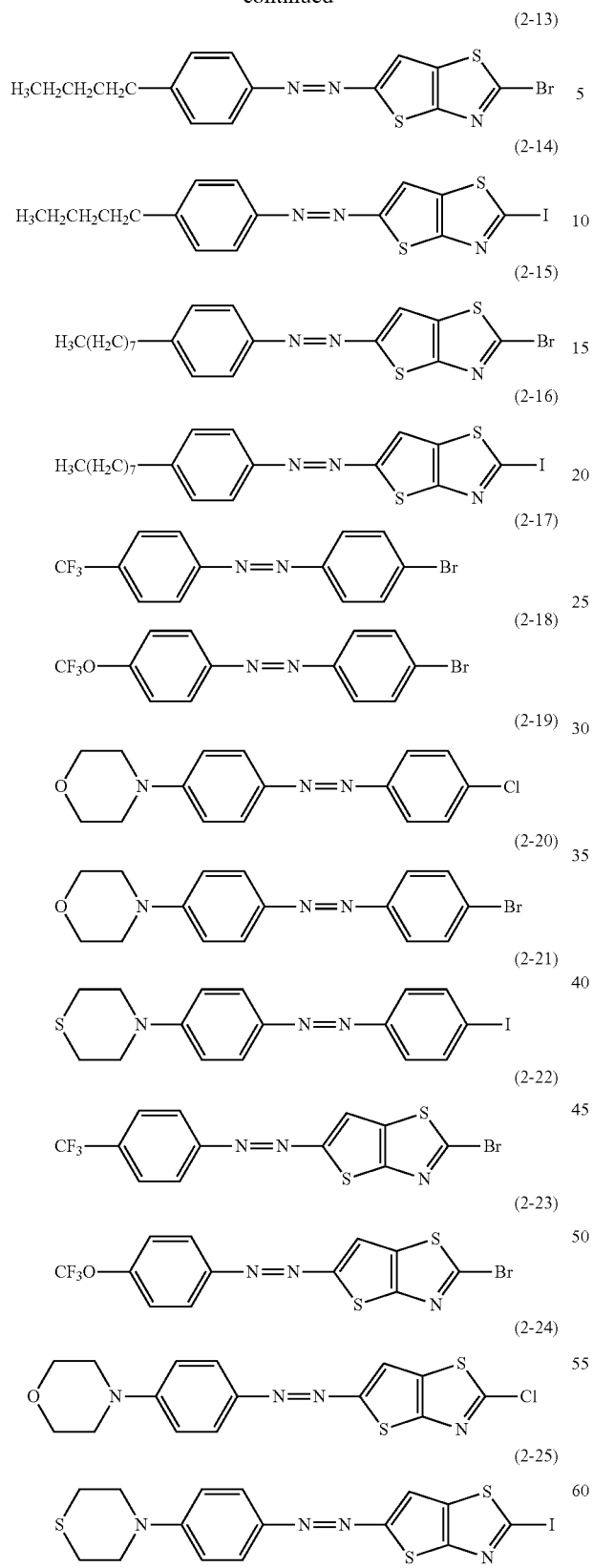
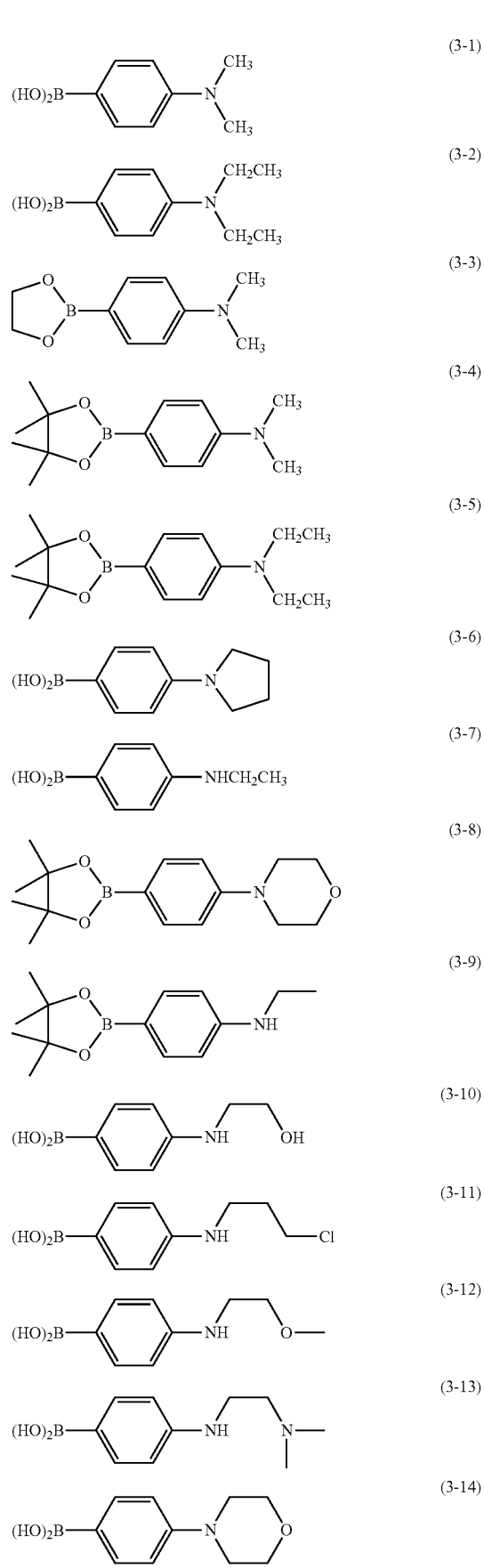
The preferable compound (3) may specifically be compounds represented by the following formula (3-1) to formula (3-15).

-continued

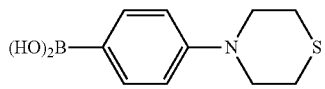
(3-15)

The compound (3) may be a commercialized compound or may be synthesized according to the method described in Journal of Organic Chemistry, 1995, 60, 7508.

The reaction of the compound (2) and the compound (3) can be carried out, for example, according to the method described in Chemical Reviews, 1995, 95(7), 2457.

The compound (1) can be taken out, after the reaction, by a common refining operation such as re-crystallization, re-precipitation, extraction, or various types of chromatography, or by combining these refining operations.

<Compound 5>

The present invention also relates to the compound represented by the formula (5):

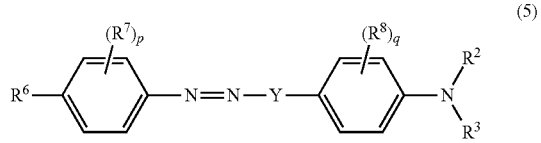
(5)

wherein, Y represents a group represented by the formula (Y1) or the formula (Y2)

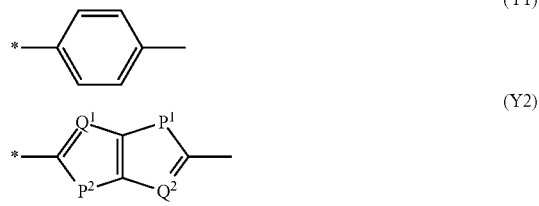
(Y1)

(Y2)

(* shows a bonding site to N;

$P^1$ and $P^2$ each independently represent a sulfur atom, an oxygen atom or $-NR^{10}-$, $R^{10}$ represents a hydrogen atom or an alkyl group having 1 to 4 carbon atoms;

$Q^1$ and $Q^2$ each independently represent a nitrogen atom or $=CH-$);

in the formula (5), $R^2$, $R^3$, $R^7$, $R^8$, p, and q mean as defined in the formula (1);

$R^6$ represents an alkyl group having 2 to 20 carbon atoms, an alkoxy group having 1 to 20 carbon atoms, or $-N(R)(R^0)$; R and $R^0$ each independently represent a hydrogen atom or an alkyl group having 1 to 10 carbon atoms, or R and $R^0$ are bonded together to form a ring together with the nitrogen atom to which R and $R^0$ are bonded; one or more hydrogen atoms constituting the alkyl group having 2 to 20 carbon atoms, the alkoxy group having 1 to 20 carbon atoms, and the alkyl group having 1 to 10 carbon atoms are independently optionally substituted with an atom or a group selected from the group consisting of a halogen atom, a hydroxyl group and an optionally substituted amino group; the alkyl group having 2 to 20 carbon atoms, the alkoxy group having 1 to 20 carbon atoms, and the alkyl group having 1 to 10 carbon atoms each optionally have an ether linkage (—O—) between carbon atoms constituting them.

The azo group of the compound represented by the formula (5) is preferable to be a trans-form. Hereinafter, the compound represented by the formula (5) may be sometimes referred to as a compound (5).

The alkyl group having 2 to 20 carbon atoms represented by $R^6$ may be a linear or branched alkyl group such as ethyl group, n-propyl group, isopropyl group, n-butyl group, isobutyl group, tert-butyl group, n-pentyl group, isopentyl group, neopentyl group, n-hexyl group, n-heptyl group, n-octyl group, n-nonyl group or n-decyl group.

One or more hydrogen atoms constituting the alkyl group having 2 to 20 carbon atoms are independently optionally substituted with a halogen atom, a hydroxyl group, or an optionally substituted amino group, and each optionally have an ether linkage between carbon atoms constituting them. Examples of the alkyl group having 2 to 20 carbon atoms may include those described as examples of $R^1$ in the compound (1).

The alkoxy group having 1 to 20 carbon atoms and $-N(R)(R^0)$ represented by $R^6$ may be the same as those described in the compound (1).

In the formula (5), p and q each independently represent an integer of 0 to 2, and preferably both 0. In this case, the compound (5) becomes a compound represented by the formula (5a):

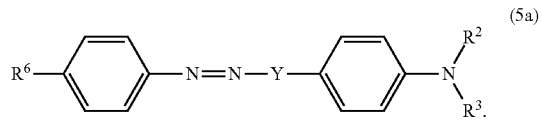
(5a)

Preferable compounds as the compound (5) are the same as those listed as the compound (1).

The compound (5) can be produced and obtained by the same method as that in the compound (1).

The compounds (1) and (5) have maximum absorption in a wavelength range of 350 nm to 550 nm, preferably in a wavelength range of 390 nm to 550 nm, more preferably in a wavelength range of 390 nm to 500 nm, furthermore preferably in a wavelength range of 400 nm to 500 nm, still more preferably in a wavelength range of 410 nm to 490 nm, and even more preferably in a wavelength range of 420 nm to 480 nm. These compounds are compounds functioning as dichroic dyes. Particularly, a polarizing film obtained by orienting the compounds together with a polymerizable liquid crystal compound exhibits high-order dichroism.

<Polymerizable Liquid Crystal Compound>

A polymerizable liquid crystal compound is a compound which has a polymerizable group in a molecule and can show a liquid crystal phase by being oriented. The compound is preferably capable of showing a liquid crystal phase by being oriented by itself.

The polymerizable group means a group involved in polymerization reaction and is preferably a photopolymerizable group. Herein, the polymerizable group refers to a group which can be involved in polymerization reaction by an active radical or an acid generated from a polymerization initiator described below. The polymerizable group may be a vinyl group, a vinyloxy group, a 1-chlorovinyl group, an isopropenyl group, a 4-vinylphenyl group, an acryloyloxy group, a methacryloyloxy group, an oxiranyl group, an oxetanyl group, etc. Especially, an acryloyloxy group, a methacryloyloxy group, a vinyloxy group, an oxiranyl group and an oxetanyl group are preferable, and an acryloyloxy group is more preferable.

The polymerizable liquid crystal compound may be of a thermotropic liquid crystal type or of a lyotropic liquid crystal type.

The polymerizable liquid crystal compound may be those which show a nematic liquid crystal phase, a smectic liquid crystal phase, or both nematic liquid crystal phase and smectic liquid crystal phase. The polymerizable liquid crystal compound is preferable to show a smectic liquid crystal phase and more preferable to show a higher-order smectic liquid crystal phase. Use of a composition containing a polymerizable liquid crystal compound exhibiting a smectic liquid crystal phase makes it possible to provide a polarizing film excellent in polarizing performance. One kind of polymerizable liquid crystal compound or two or more kinds of polymerizable liquid crystal compounds in combination may be added to the present composition.

The compound (1) is formed from a polymerizable liquid crystal compound exhibiting a smectic liquid crystal phase, and is capable of showing high dichroism and providing a polarizing film with a high dichroic ratio even though the compound (1) is dispersed densely in molecular chains.

The higher-order smectic liquid crystal phase may be a smectic B phase, a smectic D phase, a smectic E phase, a smectic F phase, a smectic G phase, a smectic H phase, a smectic I phase, a smectic J phase, a smectic K phase, a smectic L phase, etc. Especially, a smectic B phase, a smectic F phase and a smectic I phase are preferable. If the smectic liquid crystal phase of the polymerizable liquid crystal compound is such a higher-order smectic phase, it is possible to produce a polarizing film with higher degree of orientation order. A polarizing film with higher degree of orientation order, which is produced from a polymerizable liquid crystal compound having a higher-order smectic liquid crystal phase, exhibits a Bragg peak derived from higher-order structure of a hexatic phase or a crystal phase in x-ray diffraction measurement. The Bragg peak is a peak derived from a surface periodic structure of molecule orientation. The periodic interval of a polarizing film produced from the present composition is preferably 3.0 to 5.0 angstroms (0.30 nm to 0.50 nm).

The kind of a liquid crystal phase shown by a polymerizable liquid crystal compound can be confirmed, for example, by the following manner. A proper substrate is made available, a solution containing a polymerizable liquid crystal compound and a solvent is applied to the substrate to form a coating film, and thereafter, the solvent contained in the coating film is removed by heat treatment or vacuum treatment. Successively, the coating film formed on the substrate is heated to an isotropic phase temperature and gradually cooled to generate a liquid crystal phase, which is inspected by texture observation with a polarizing microscope, x-ray diffraction measurement, or differential scanning calorimetry. In this inspection, for example, it can be confirmed that a nematic liquid crystal phase is shown by cooling to a first temperature and a smectic liquid phase is shown by gradually cooling to a second temperature.

The polymerizable liquid crystal composition is preferably a compound represented by the formula (4). Hereinafter, the compound represented by the formula (4) may be sometimes referred to as a compound (4):

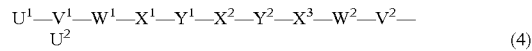
(4)

wherein $X^1$, $X^2$ and $X^3$ each independently represent an optionally substituted 1,4-phenylene group or an optionally substituted cyclohexane-1,4-diyl group, provided that at least one of $X^1$, $X^2$ and $X^3$ is an optionally substituted 1,4-phenylene group; the methylene (—$CH_2$—) constituting the cyclohexane-1,4-diyl group is optionally substituted with —O—, —S— or —NR—; R represents an alkyl or phenyl group having 1 to 6 carbon atoms;

$Y^1$ and $Y^2$ each independently represent —$CH_2CH_2$—, —$CH_2O$—, —COO—, —OCOO—, a single bond, —N═N—, —$CR^a$═$CR^b$—, —C≡C— or —$CR^a$═N—; $R^a$ and $R^b$ each independently represent a hydrogen atom or an alkyl group having 1 to 4 carbon atoms;

$U^1$ represents a hydrogen atom or a polymerizable group; $U^2$ represents a polymerizable group;

$W^1$ and $W^2$ each independently represent a single bond, —O—, —S—, —COO—, or —OCOO—;

$V^1$ and $V^2$ each independently represent an optionally substituted alkanediyl group having 1 to 20 carbon atoms where —$CH_2$— constituting the alkanediyl group are optionally substituted with —O—, —S— or —NH—.

In the compound (4), it is preferable that at least one of $X^1$, $X^2$, and $X^3$ is an optionally substituted 1,4-phenylene group.

The optionally substituted 1,4-phenylene group is preferably an unsubstituted 1,4-phenylene group. The optionally substituted cyclohexane-1,4-diyl group is preferably an optionally substituted trans-cyclohexane-1,4-diyl group; and the optionally substituted trans-cyclohexane-1,4-diyl group is more preferably an unsubstituted trans-cyclohexane-1,4-diyl group.

The optionally substituted 1,4-phenylene group or the optionally substituted cyclohexane-1,4-diyl group may arbitrary have alkyl group having 1 to 4 carbon atoms such as methyl group, ethyl group and butyl group; cyano group; halogen atom; etc. as substituents.

$Y^1$ is preferably —$CH_2CH_2$—, —COO— or a single bond, and $Y^2$ is preferably —$CH_2CH_2$— or —$CH_2O$—.

$U^2$ is a polymerizable group. $U^1$ is a hydrogen atom or a polymerizable group and preferably a polymerizable group. $U^1$ and $U^2$ are both preferably a polymerizable group, and more preferably a photopolymerizable group. A polymerizable liquid crystal compound having a photopolymerizable group is advantageous in terms of being capable of polymerization under lower temperature conditions.

The polymerizable groups represented by $U^1$ and $U^2$ may be different from each other, but are preferably the same. The polymerizable group may be a vinyl group, a vinyloxy group, a 1-chlorovinyl group, an isopropenyl group, a 4-vinylphenyl group, an acryloyloxy group, a methacryloyloxy group, an oxiranyl group, an oxetanyl group, etc. Especially, an acryloyloxy group, a methacryloyloxy group, a vinyloxy group, an oxiranyl group and an oxetanyl group are preferable, and an acryloyloxy group is more preferable.

The alkanediyl group represented by $V^1$ and $V^2$ may be a methylene group, an ethylene group, a propane-1,3-diyl group, a butane-1,3-diyl group, a butane-1,4-diyl group, a pentane-1,5-diyl group, a hexane-1,6-diyl group, a heptane-1,7-diyl group, an octane-1,8-diyl group, a decane-1,10-diyl group, a tetradecane-1,14-diyl group, an icosane-1,20-diyl group, etc. $V^1$ and $V^2$ are preferably an alkanediyl group having 2 to 12 carbon atoms and more preferably an alkanediyl group having 6 to 12 carbon atoms.

The optionally substituted alkanediyl group having 1 to 20 carbon atoms may have a cyano group, a halogen atom etc. as a substituent. The alkanediyl group is preferably an unsubstituted alkanediyl group, and more preferably a linear unsubstituted alkanediyl group.

Preferably, $W^1$ and $W^2$ are each independently a single bond or —O—.

Specific examples of the compound (4) may include compounds represented by the formula (4-1) to the formula (4-43). When the compound (4) has a cyclohexane-1,4-diyl group, the cyclohexane-1,4-diyl group is preferably a trans-form.
(4-1)
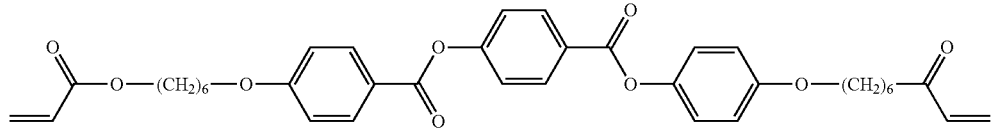
(4-2)
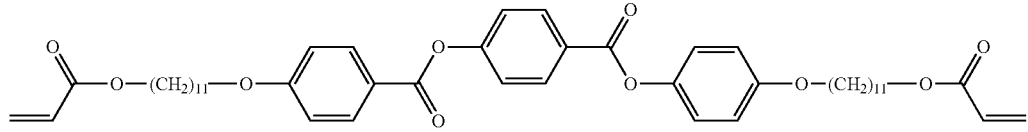
(4-3)
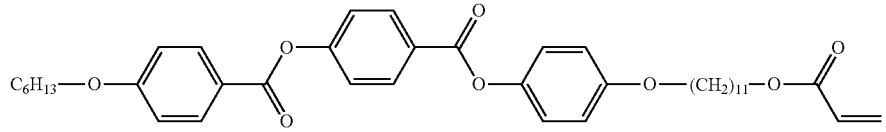
(4-4)
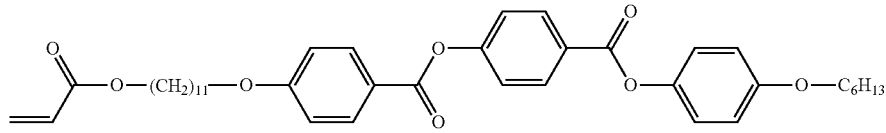
(4-5)
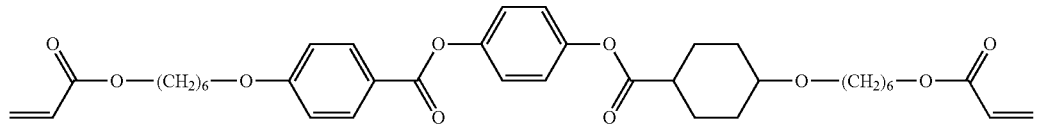
(4-6)
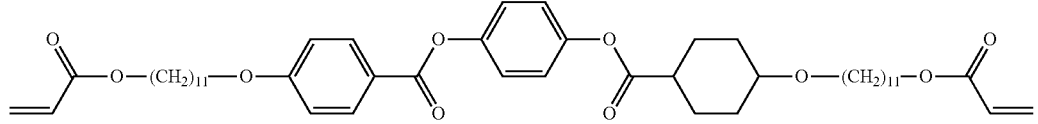
(4-7)
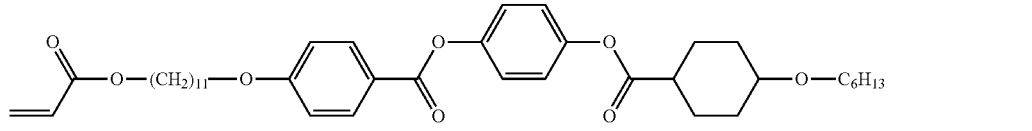
(4-8)
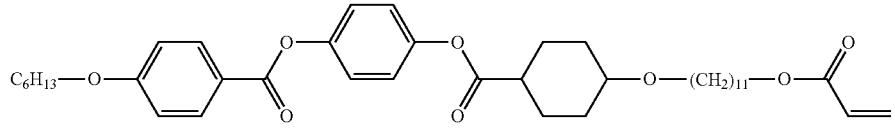
(4-9)
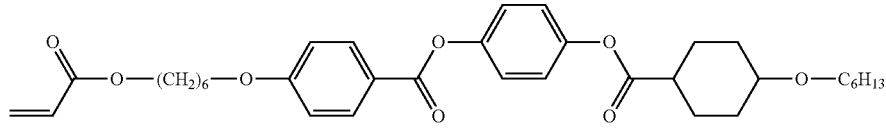
(4-10)
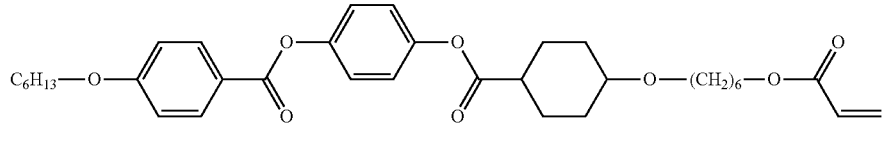

-continued
(4-11)
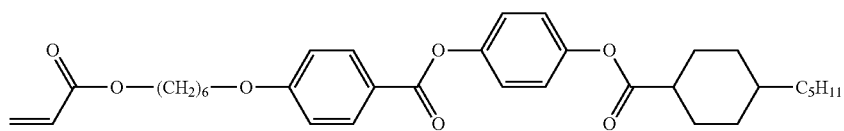
(4-12)
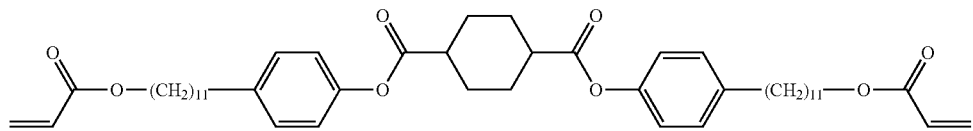
(4-13)
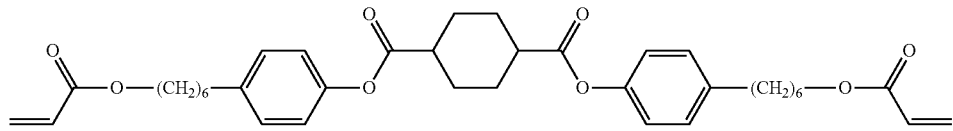
(4-14)
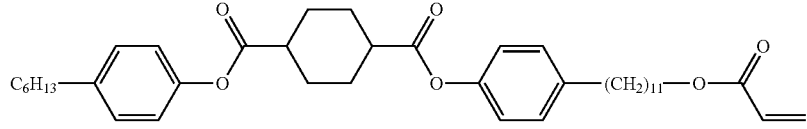
(4-15)
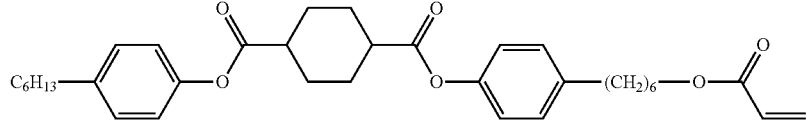
(4-16)
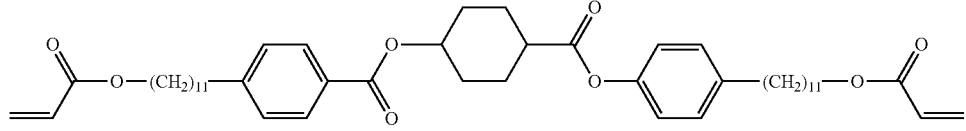
(4-17)
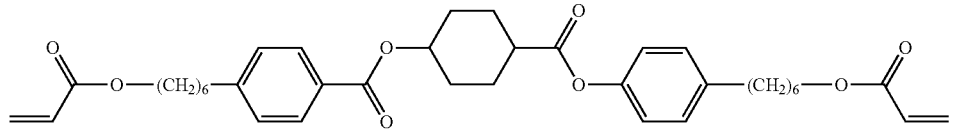
(4-18)
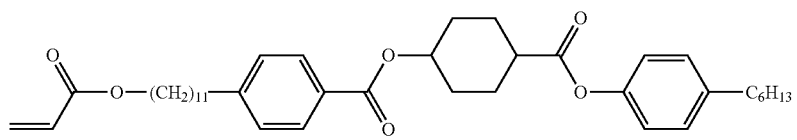
(4-19)
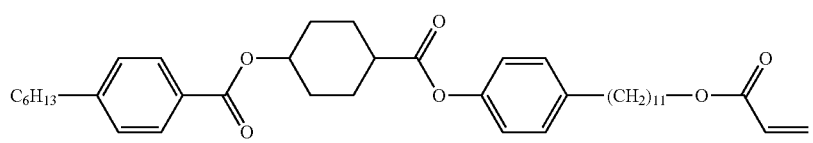
(4-20)
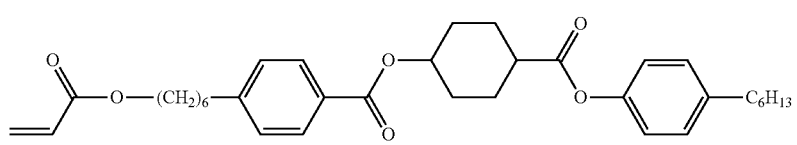
(4-21)
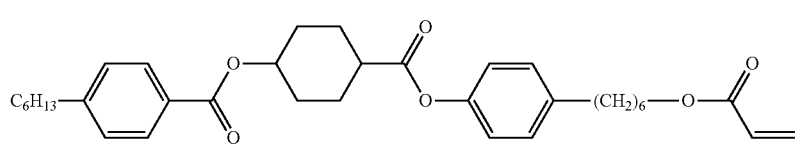

-continued
(4-22)
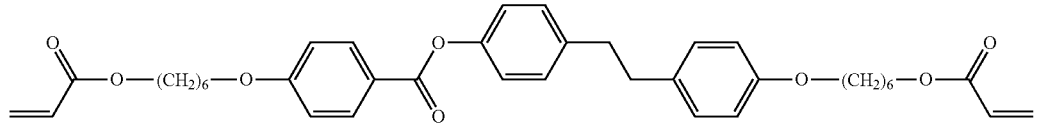
(4-23)
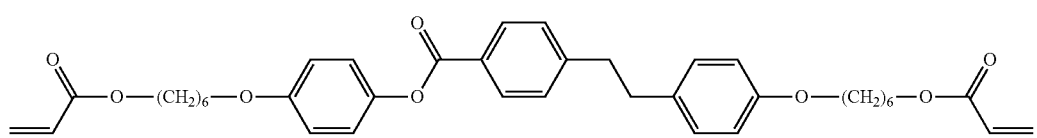
(4-24)
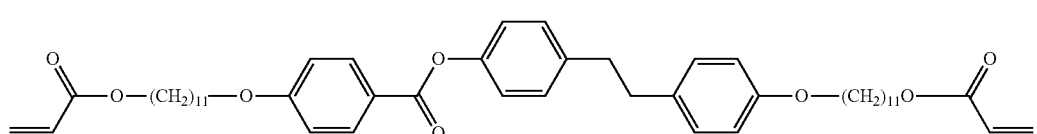
(4-25)
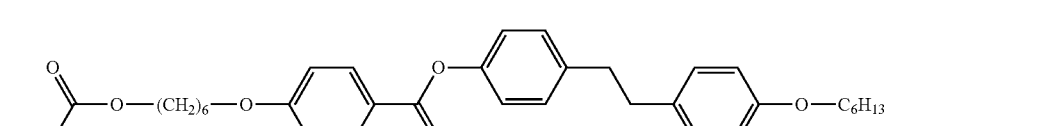
(4-26)
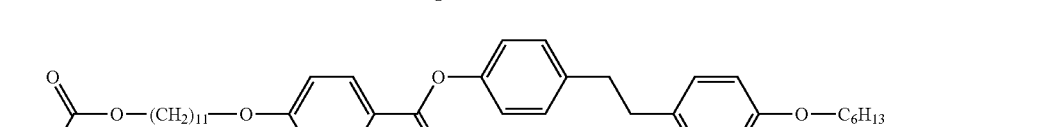
(4-27)
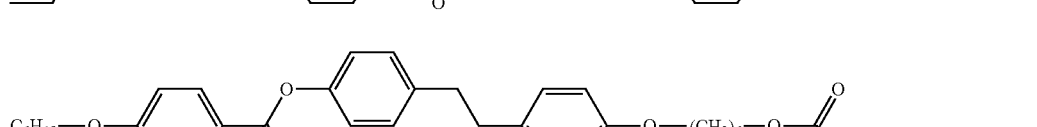
(4-28)
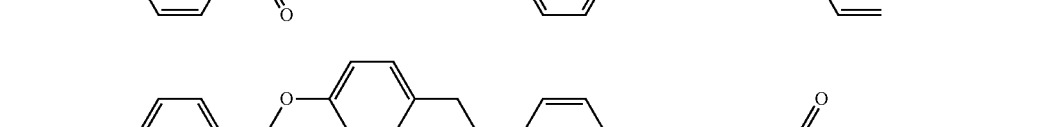
(4-29)
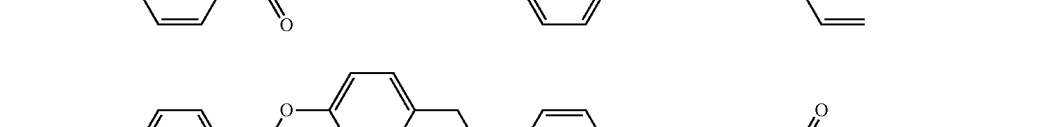
(4-30)
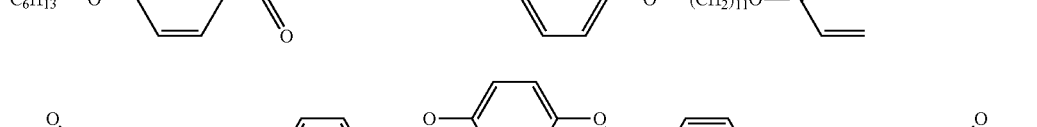
(4-31)
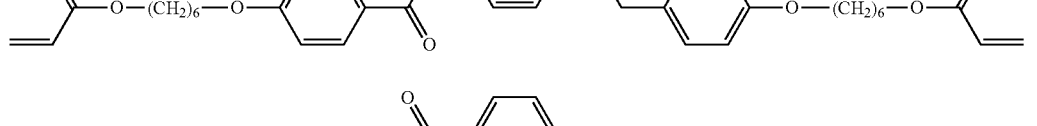
(4-32)
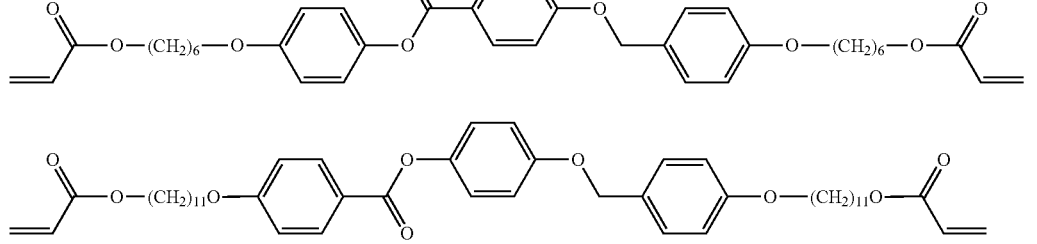

-continued
(4-33)
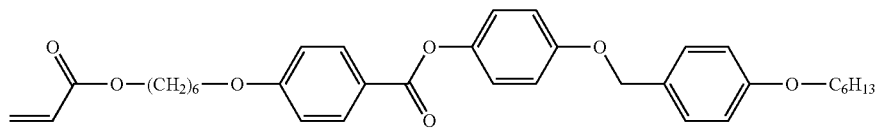
(4-34)
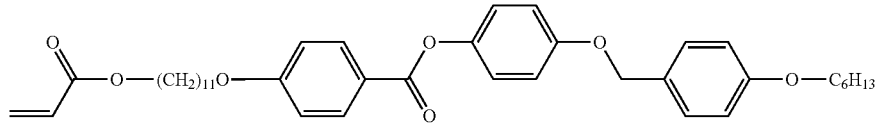
(4-35)
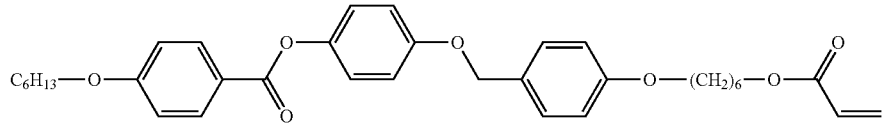
(4-36)
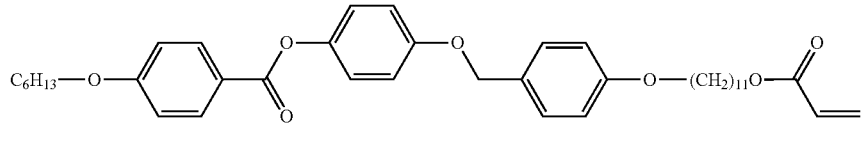
(4-37)
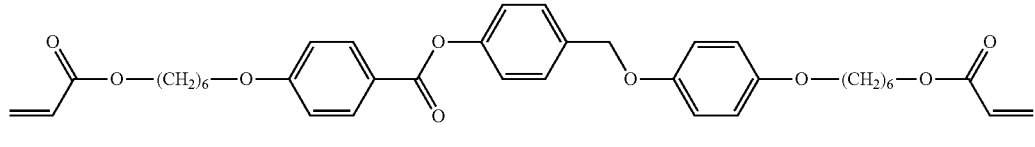
(4-38)
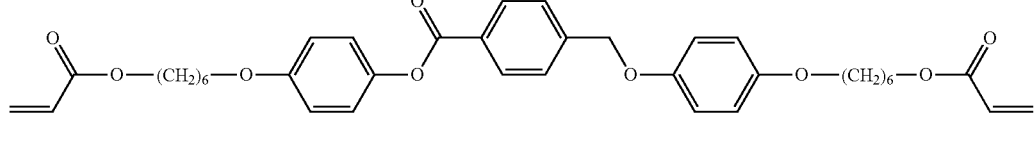
(4-39)
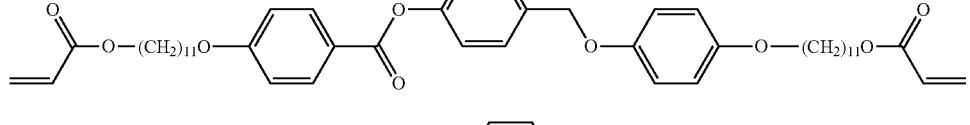
(4-40)
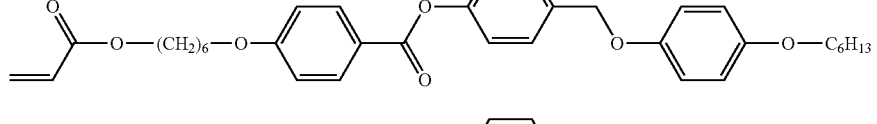
(4-41)
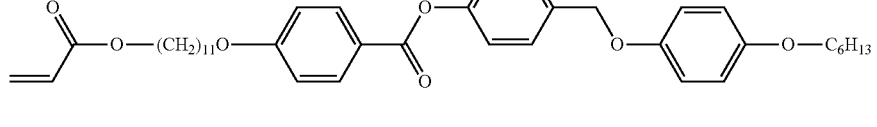
(4-42)
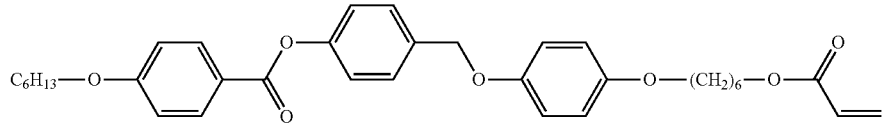
(4-43)
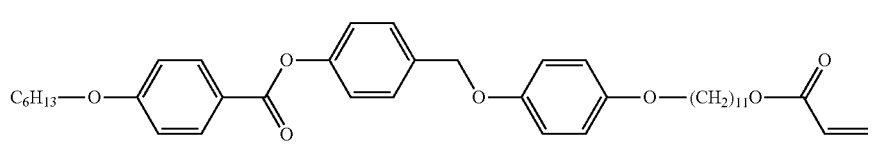

Especially, the compound (4) is preferably at least one compound selected from the group consisting of compounds represented by the formula (4-5), the formula (4-6), the formula (4-7), the formula (4-8), the formula (4-9), the formula (4-10), the formula (4-11), the formula (4-12), the formula (4-13), the formula (4-14), the formula (4-15), the formula (4-22), the formula (4-24), the formula (4-25), the formula (4-26), the formula (4-27), the formula (4-28) and the formula (4-29).

The examples of the compound (4) may be used alone or in combination for the present composition. When two or more kinds of polymerizable liquid crystal compounds are used in combination, it is preferable that at least one kind is the compound (4), and it is more preferable that two or more kinds are the compound (4). Combination use may sometimes retain a liquid crystal phase temporarily even at a liquid crystal-crystal phase transition temperature or lower. When two kinds of polymerizable liquid crystal compounds are used in combination, the mixing ratio is usually 1:99 to 50:50, preferably 5:95 to 50:50, and more preferably 10:90 to 50:50.

The compound (4) can be produced by a conventionally known method described in, for example, Lub et al. Recl. Tray. Chim. Pays-Bas, 115, 321-328 (1996) or Japanese Patent No. 4719156.

The content of the polymerizable liquid crystal compound in the present composition is preferably 70 to 99.5 parts by mass, more preferably 80 to 99 parts by mass, furthermore preferably 80 to 94 parts by mass, and even more preferably 80 to 90 parts by mass based on 100 parts by mass of the solid matter of the present composition in terms of improvement in orientation of the polymerizable liquid crystal compound. Herein, the solid matter refers to the total amount of the components of the present composition from which the solvent is excluded.

The present composition is preferable to further contain a polymerization initiator and a solvent, and may also contain a photosensitizer, a polymerization inhibitor and a leveling agent.

The content of the compound (1) in the present composition is usually 50 parts by mass or less, preferably 0.1 parts by mass or more and 10 parts by mass or less, more preferably 0.1 parts by mass or more and 5 parts by mass or less based on 100 parts by mass of the polymerizable liquid crystal compound. If the content of the compound (1) is 50 parts by mass or less based on 100 parts by mass of the polymerizable liquid crystal compound, a polarizing film with little orientation disorder of the polymerizable liquid crystal compound and that of the compound (1) tends to be obtained, and therefore it is preferable.

[Solvent]

The solvent is preferable to be a solvent in which the polymerizable liquid crystal compound and the compound (1) can completely be dissolved. The solvent is also preferable to be a solvent inactive to the polymerization reaction of the polymerizable liquid crystal compound.

The solvent may be alcohol solvents such as methanol, ethanol, ethylene glycol, isopropyl alcohol, propylene glycol, ethylene glycol methyl ether, ethylene glycol butyl ether and propylene glycol monomethyl ether; ester solvents such as ethyl acetate, butyl acetate, ethylene glycol methyl ether acetate, γ-butyrolactone, propylene glycol methyl ether acetate and ethyl lactate; ketone solvents such as acetone, methyl ethyl ketone, cyclopentanone, cyclohexanone, 2-heptanone and methyl isobutyl ketone; aliphatic hydrocarbon solvents such as pentane, hexane and heptane; aromatic hydrocarbon solvents such as toluene and xylene; nitrile solvents such as acetonitrile; ether solvents such as tetrahydrofuran and dimethoxyethane; chlorine-containing solvents such as chloroform and chlorobenzene; etc. These solvents may be used alone or a plurality of these solvents may be used in combination.

When the present composition contains a solvent, the content of the solvent is preferably 50 to 98% by mass based on the total mass of the present composition. In other words, the solid matter in the present composition is preferably 2 to 50% by mass. If the mass of the solid matter is 50% by mass or less, the viscosity of the present composition is lowered so that the thickness of the polarizing film can be substantially even. Because the polarizing film has a substantially even thickness, unevenness tends to hardly occur in the polarizing film. The mass of the solid matter may be determined in consideration of the thickness of the polarizing film to be produced.

<Polymerization Initiator>

A polymerization initiator is a compound capable of starting the polymerization reaction of a polymerizable liquid crystal compound. A photopolymerization initiator generating an active radical by light action is preferable as the polymerization initiator.

Examples of the polymerization initiator may include a benzoin compound, a benzophenone compound, an alkylphenone compound, an acylphosphine oxide compound, a triazine compound, an iodonium salt, a sulfonium salt, etc.

Examples of the benzoin compound may include benzoin, benzoin methyl ether, benzoin ethyl ether, benzoin isopropyl ether, benzoin isobutyl ether, etc.

Examples of the benzophenone compound may include benzophenone, methyl o-benzoyl benzoate, 4-phenylbenzophenone, 4-benzoyl-4'-methyldiphenyl sulfide, 3,3',4,4'-tetra(tert-butyl peroxycarbonyl)benzophenone, 2,4,6-trimethylbenzophenone, etc.

Examples of the alkylphenone compound may include diethoxy acetophenone, 2-methyl-2-morpholino-1-(4-methyl thiophenyl)propan-1-one, 2-benzyl-2-dimethylamino-1-(4-morpholinophenyl)butan-1-one, 2-hydroxy-2-methyl-1-phenylpropan-1-one, 1,2-diphenyl-2,2-dimethoxyethan-1-one, 2-hydroxy-2-methyl-1-[4-(2-hydroxyethoxy)phenyl]propan-1-one, 1-hydroxycyclohexyl phenyl ketone, an oligomer of 2-hydroxy-2-methyl-1-[4-(1-methylvinyl)phenyl]propan-1-one, etc.

Examples of the acylphosphine oxide compound may include 2,4,6-trimethylbenzoyldiphenylphosphine oxide, bis(2,4,6-trimethylbenzoyl)phenylphosphine oxide, etc.

Examples of the triazine compound may include 2,4-bis(trichloromethyl)-6-(4-methoxyphenyl)-1,3,5-triazine, 2,4-bis(trichloromethyl)-6-(4-methoxynaphthyl)-1,3,5-triazine, 2,4-bis(trichloromethyl)-6-(4-methoxystyryl)-1,3,5-triazine, 2,4-bis(trichloromethyl)-6-[2-(5-methylfuran-2-yl)ethenyl]-1,3,5-triazine, 2,4-bis(trichloromethyl)-6-[2-(furan-2-yl)ethenyl]-1,3,5-triazine, 2,4-bis(trichloromethyl)-6-[2-(4-diethylamino-2-methylphenyl) ethenyl]-1,3,5-triazine, 2,4-bis(trichloromethyl)-6-[2-(3,4-dimethoxyphenyl)ethenyl]-1,3,5-triazine, etc.

Examples of the iodonium salt and the sulfonium salt may include salts represented by the following formula.

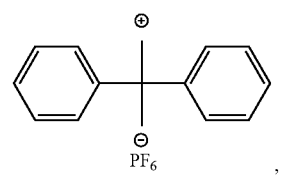

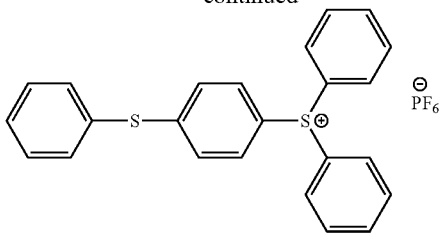

One kind of polymerization initiator may be used alone or two or more kinds of polymerization initiators may be used in combination.

Commercialized polymerization initiators may be used. The commercialized polymerization initiator may be Irgacure (registered trade name) 907, 184, 651, 819, 250 and 369 (manufactured by Ciba Specialty Chemicals Inc.); Seikuol (registered trade name) BZ, Z and BEE (manufactured by Seiko Chemical Co., Ltd); Kayacure (registered trade name) BP100 and UVI-6992 (manufactured by The Dow Chemical Company); Adeka Optomer SP-152 and SP-170 (manufactured by ADEKA); TAZ-A and TAZ-PP (manufactured by DKSH Japan K.K); TAZ-104 (manufactured by Sanwa Chemical Co., Ltd.); etc.

When the present composition contains a polymerization initiator, the content of the polymerization initiator in the present composition is usually 0.1 to 30 parts by mass, preferably 0.5 to 10 parts by mass, and more preferably 0.5 to 8 parts by mass based on 100 parts by mass of the polymerizable liquid crystal compound in terms of hardly causing orientation disorder of the polymerizable liquid crystal compound.

[Photosensitizer]

When the present composition contains a photopolymerization initiator, the present composition is preferable to contain a photosensitizer. When the present composition contains a photopolymerization initiator and a photosensitizer, the polymerization reaction of the polymerizable liquid crystal compound contained in the present composition tends to be promoted. The photosensitizer may be xanthone compounds such as xanthone and thioxanthone (e.g., 2,4-diethylthioxanthone, 2-isopropylthioxanthone); anthracene compounds such as anthracene and an alkoxy-containing anthracene (e.g., dibutoxyanthracene); phenothiazine, rubrene, etc.

When the present composition contains a photosensitizer, the content of the photosensitizer in the present composition is preferably 0.1 to 30 parts by mass, more preferably 0.5 to 10 parts by mass, and furthermore preferably 0.5 to 8 parts by mass based on 100 parts by mass of the polymerizable liquid crystal compound.

<Polymerization Inhibitor>

The polymerization inhibitor may be radical scavengers such as hydroquinone, alkoxy-containing hydroquinone, alkoxy-containing catechol (e.g., butyl catechol), pyrogallol and 2,2,6,6-tetramethyl-1-piperidinyloxy radial; thiophenols; β-naphthylamines; β-naphthols; etc.

Addition of a polymerization inhibitor to the present composition can control the degree of promoting the polymerization reaction of the polymerizable liquid crystal compound.

When the present composition contains a polymerization inhibitor, the content of the polymerization inhibitor in the present composition is preferably 0.1 to 30 parts by mass, more preferably 0.5 to 10 parts by mass, and furthermore preferably 0.5 to 8 parts by mass based on 100 parts by mass of the polymerizable liquid crystal compound.

<Leveling Agent>

A leveling agent has a function of adjusting the fluidity of the present composition and leveling a coating film obtained by applying the present composition in a higher manner. An example thereof may include a surfactant. A preferable leveling agent may be a leveling agent containing a polyacrylate compound as a main component and a leveling agent containing a fluorine atom-containing compound as a main component.

The leveling agent containing a polyacrylate compound as a main component may be BYK-350, BYK-352, BYK-353, BYK-354, BYK-355, BYK-358N, BYK-361N, BYK-380, BYK-381 and BYK-392 (manufactured by BYK-Chemie GmbH).

The leveling agent containing a fluorine atom-containing compound as a main component may be Megafac (registered trade name) R-08, R-30, R-90, F-410, F-411, F-443, F-445, F-470, F-471, F-477, F-479, F-482 and F-483 (manufactured by DIC Corporation); Surflon (registered trade name) S-381, S-382, S-383, S-393, SC-101, SC-105, KH-40 and SA-100 (AGC Seimi Chemical Co., Ltd.); E1830 and E5844 (manufactured by Daikin Fine Chemical Kenkyusho, K.K.); EFTOP EF301, EF303, EF351 and EF352 (manufactured by Mitsubishi Materials Electronic Chemicals Co., Ltd.); etc.

When the present composition contains a leveling agent, the content of the leveling agent is preferably 0.3 parts by mass or more and 5 parts by mass or less, and more preferably 0.5 parts by mass or more and 3 parts by mass or less based on 100 parts by mass of the polymerizable liquid crystal compound.

If the content of the leveling agent is in the above-mentioned range, horizontal orientation of the polymerizable liquid crystal compound is made easy, and the polarizing film to be obtained tends to be more smooth. If the content of the leveling agent to the polymerizable liquid crystal compound exceeds the above-mentioned range, the polarizing film to be obtained tends to be uneven. One kind of leveling agent may be used and two or more kinds of leveling agents may be used in combination.

<Method for Producing Polarizing Film>

A polarizing film which is formed from the present composition and which contains the compound (1) can be obtained by applying the present composition. Preferably, the polarizing film can be produced by a production method including the following steps (1) to (3). A polarizing film containing the compound (5) can be also obtained by applying the compound (5). Similarly to the method for producing a polarizing film from the present composition, a polarizing film can be obtained by applying a composition containing the compound (5) and a polymerizable liquid crystal compound, and preferably can be produced by a production method including the following steps (1) to (3). Hereinafter, the polarizing film formed from the present composition and the polarizing film containing the compound (5) may be both sometimes referred to as the present polarizing film.

(1) A step of applying the present composition to a surface of a substrate or a surface of a substrate on which an orientation film is formed.

(2) A step of orienting the polymerizable liquid crystal compound and the compound (1) contained in the applied composition.

(3) A step of polymerizing the oriented polymerizable liquid crystal compound by irradiation with activation energy rays.

<Step (1)>
<Substrate>

A substrate may be either a glass substrate or a resin substrate, and is preferably a resin substrate. Use of a film substrate made of resin makes it possible to obtain a thin polarizing plate.

The resin substrate is preferably a transparent resin substrate. The transparent resin substrate means a substrate having translucency for transmitting light particularly visible light, and the translucency means a characteristic of 80% or higher visibility correcting transmittance to light rays with a wavelength of 380 nm to 780 nm.

The substrate is preferably a retardation film having a ¼ wavelength plate function (hereinafter, may be sometimes referred to as ¼ wavelength plate). Use of a ¼ wavelength plate for the substrate makes it possible to obtain a circularly polarizing plate.

In this case, it is preferable to laminate the polarizing film on the substrate in such a manner that the angle between the transmission axis of the polarizing film and the slow axis (optical axis) of the ¼ wavelength plate becomes substantially 45°. The term "substantially 45°" usually ranges 45±5°. A polarizing film having a function as an optical compensation film can be obtained by making the optical axes of the polarizing film and the ¼ wavelength plate coincident with each other or orthogonal to each other.

The ¼ wavelength plate usually have an optical characteristic represented by the inequality (40) and preferably have an optical characteristic represented by the inequality (40-1).

$$100 \text{ nm} < Re(550) < 160 \text{ nm} \quad (40)$$

$$130 \text{ nm} < Re(550) < 150 \text{ nm} \quad (40\text{-}1)$$

Re (550) represents an in-plane retardation value to light with a wavelength of 550 nm.

Further, the ¼ wavelength plate is preferable to have a reverse wavelength dispersion characteristic. The reverse wavelength dispersion characteristic means that an in-plane retardation value at a shorter wavelength is higher than an in-plane phase retardation at longer wavelength, and the reverse wavelength dispersion characteristic preferably satisfies optical characteristics represented by the inequality (50) and the inequality (51). $Re(\lambda)$ represents an in-plane retardation value to light with a wavelength of $\lambda$ nm. A circularly polarizing plate including a ¼ wavelength plate having optical characteristics represented by the inequality (50) and the inequality (51) is provided with a characteristic of uniform polarization conversion to light with every wavelength in a visible light region, and accordingly the circularly polarizing plate tends to be excellent in reflection prevention characteristic.

$$Re(450)/Re(550) \leq 1.00 \quad (50)$$

$$1.00 \leq Re(630)/Re(550) \quad (51)$$

The substrate may also be a retardation film having a ½ wavelength plate function.

Examples of the resin constituting the substrate may include polyolefins such as polyethylene, polypropylene and norbornene-type polymer; cyclic olefin-type resin; polyvinyl alcohol; polyethylene terephthalate; polymethacrylic acid ester; polyacrylic acid ester; cellulose esters such as triacetyl cellulose, diacetyl cellulose and cellulose acetate propionate; polyethylene naphthalate; polycarbonate; polysulfone; polyether sulfone; polyether ketone; polyphenylene sulfide; polyphenylene oxide; etc. Preferred are cellulose ester, cyclic olefin-type resin, polycarbonate, polyether sulfone, polyethylene terephthalate and polymethacrylic acid ester.

A cellulose ester is cellulose in which at least a part of hydroxyl group in cellulose is esterified, and the cellulose ester is made available in markets. A substrate containing a cellulose ester is also made available in markets. Examples of the commercialized cellulose ester-containing substrate may be Fujitack (registered trade name) film (manufactured by Fuji Photo Film Co., Ltd.); KC8UX2M, KC8UY and KC4UY (manufactured by Konica Minolta Opto Products Co., Ltd.); etc.

A cyclic olefin-type resin may include polymers of cyclic olefins such as norbornene and polycyclic norbornane-type monomers and copolymers thereof. The cyclic olefin-type resin may have an open-ring structure, or may be a hydrogenated cyclic olefin-type resin having an open-ring structure. The cyclic olefin-type resin may contain a structural unit derived from a chain olefin and an aromatic vinyl compound to an extent that the transparency is not significantly deteriorated and hygroscopicity is not significantly increased. The cyclic olefin-type resin may also have a polar group in its molecule.

The chain olefin may be ethylene, propylene etc., and the aromatic vinyl compound may be styrene, α-methylstyrene, an alkyl-substituted styrene, etc.

When the cyclic olefin-type resin is a copolymer of cyclic olefin with chain olefin or aromatic vinyl compound, the content of the structural unit derived from the cyclic olefin is usually 50% by mole or lower and preferably 15 to 50% by mole in the entire structure units of the copolymer.

When the cyclic olefin-type resin is a terpolymer of cyclic olefin, chain olefin, and aromatic vinyl compound, the content of the structural unit derived from the chain olefin is usually 5 to 80% by mole in the entire structure units of the terpolymer and the content of the structural unit derived from the aromatic vinyl compound is usually 5 to 80% by mole in the entire structure units of the terpolymer. The terpolymer has an advantage such that the use amount of cyclic olefin with high cost can be relatively lowered.

The cyclic olefin-type resin is made available in markets. The commercialized cyclic olefin-type resin may be Topas (registered trade name) (manufactured by Ticona), Arton (registered trade name) (manufactured by JSR Corporation), ZEONOR (registered trade name) (manufactured by ZEON Corporation), ZEONEX (registered trade name) (manufactured by ZEON Corporation), Apel (registered trade name) (manufactured by Mitsui Chemical Co., Ltd.), etc. The cyclic olefin-type resin may be formed into a film by a conventionally known method such as a solvent casting method or a melt extrusion method to obtain a substrate.

The commercialized substrate containing a cyclic olefin-type resin may be ESCENA (registered trade name) (manufactured by Sekisui Chemical Co., Ltd.), SCA 40 (registered trade name) (manufactured by Sekisui Chemical Co., Ltd.), ZEONOR Film (registered trade name) (manufactured by Optes Inc.), Arton film (registered trade name) (manufactured by JSR Corporation), etc.

The substrate may be subjected to surface treatment. Examples of method for the surface treatment may include a method for treating the substrate surface with corona or plasma under an atmosphere from vacuum to atmospheric pressure; a method for treating the substrate surface with laser; a method for treating the substrate surface with ozone; a method for treating the substrate surface by saponification; a method for treating the substrate surface with flame; a method for applying a coupling agent to the substrate surface; a method for treating the substrate surface with primer; a graft polymerization method in which a reactive monomer or a polymer having reactivity is attached to the substrate surface and thereafter reaction is caused by radiation or by plasma or ultraviolet irradiation; etc. Especially, a method for treating the substrate surface with corona or plasma under an atmosphere from vacuum to atmospheric pressure is preferable.

The method for treating the substrate surface with corona or plasma may be a method for carrying out surface treatment for a substrate including setting the substrate between mutually opposed electrodes and generating corona or plasma under near atmospheric pressure; a method including introducing a gas between mutually opposed electrodes, generating plasma from the gas between the electrodes, and blowing the gas in plasma state to a substrate; and a method for carrying out surface treatment for a substrate including generating glow discharge plasma in a low pressure condition.

Especially, preferred is a method for carrying out surface treatment for a substrate including setting the substrate between mutually opposed electrodes and generating corona or plasma under near atmospheric pressure or a method including introducing a gas between mutually opposed electrodes, generating plasma from the gas between the electrodes, and blowing the gas in plasma state to a substrate. The surface treatment by corona or plasma is usually carried out using a commercialized surface treatment apparatus.

The substrate may have a protection film on a surface opposite to the surface to which the present composition is applied. The protection film may be films of polyethylene, polyethylene terephthalate, polycarbonate and polyolefin as well as films in which a pressure sensitive adhesive layer is formed on the above films. Especially, polyethylene terephthalate is preferable because of slight thermal deformation at the time of being dried. When the protection film is formed on a surface opposite to the surface to which the present composition is applied, swinging of the film and weak vibration of the coated surface at the time of transportation of the substrate can be suppressed, and the evenness of the coating film can be improved.

The thickness of the substrate is more preferable to be thinner in terms of weight adequate for practical handling, but if the thickness is too thin, the strength is lowered and processability tends to become inferior. The thickness of the substrate is usually 5 to 300 μm, and preferably 20 to 200 μm.

The length of the substrate in the longitudinal direction is usually 10 to 3000 m, and preferably 100 to 2000 m. The length of the substrate in the shorter direction is usually 0.1 to 5 m, and preferably 0.2 to 2 m.

<Orientation Film>

An orientation film in the present invention is a film having an orientation regulation force for orienting a polymerizable liquid crystal compound in a desired direction.

The orientation film is preferably a film having solvent resistance such that the film is not dissolved by application of the present composition, etc., and having heat resistance in heat treatment for solvent removal or orientation of the polymerizable liquid crystal compound. The orientation film may be an orientation film containing orientational polymer, a photo-orientation film, a grooved orientation film in which irregular patterns or a plurality of grooves are formed on the surface to be oriented, etc.

The orientational polymer may be polyamides and gelatins having an amide bond in a molecule; polyimides having an imide bond in a molecule and their hydrolyzed products, polyamic acids; polyvinyl alcohols; alkyl group-modified polyvinyl alcohols; polyacrylamides; polyoxazoles; polyethyleneimines; polystyrenes; polyvinylpyrrolidones; polyacrylic acids; and polyacrylic acid esters. Especially, polyvinyl alcohols are preferable. Two or more kinds of the orientational polymers may be used in combination.

The orientation film containing orientational polymer is usually formed on a surface of a substrate by applying a composition in which the orientational polymer is dissolved in a solvent to the substrate, and removing the solvent or removing the solvent followed by rubbing (a rubbing method). Hereinafter, the composition in which the orientational polymer is dissolved in a solvent may be sometimes referred to as an orientational polymer composition.

The solvent may be water; alcohol solvents such as methanol, ethanol, ethylene glycol, isopropyl alcohol, propylene glycol, methyl cellosolve, butyl cellosolve and propylene glycol monomethyl ether; ester solvents such as ethyl acetate, butyl acetate, ethylene glycol methyl ether acetate, γ-butyrolactone, propylene glycol methyl ether acetate and ethyl lactate; ketone solvents such as acetone, methyl ethyl ketone, cyclopentanone, cyclohexanone, methyl amyl ketone and methyl isobutyl ketone; aliphatic hydrocarbon solvents such as pentane, hexane and heptane; aromatic hydrocarbon solvents such as toluene and xylene; nitrile solvents such as acetonitrile; ether solvents such as tetrahydrofuran and dimethoxyethane; and chlorinated-hydrocarbon solvents such as chloroform and chlorobenzene. These solvents may be used alone or two or more kinds thereof may be used in combination.

The concentration of the orientational polymer in the orientational polymer composition may fall within a range of completely dissolving the orientational polymer material in a solvent, and the concentration is preferably 0.1 to 20% and more preferably around 0.1 to 10% in terms of solid matter to the solvent.

A commercialized orientation film material may be used as it is as the orientational polymer composition. The commercialized orientation film material may be Sunever (registered trade name, manufactured by Nissan Chemical Industries, Ltd.), Optomer (registered trade name, manufactured by JSR Corporation), etc.

A method for applying the orientational polymer composition to a substrate may be conventionally known methods such as application methods including a spin coating method, an extrusion method, a gravure coating method, a die coating method, a slit coating method, a bar coating method, an applicator method, etc.; and printing methods including a flexographic method. When the present polarizing film is produced by a continuous production method in a Roll-to Roll manner, the application method is usually performed by a gravure coating method, a die coating method or a printing method such as a flexographic method.

A method for removing the solvent contained in the orientational polymer composition may be a natural drying method, a blow drying method, a heat drying method, a vacuum drying method, etc.

In order to provide the orientation film with orientation regulation force, rubbing is carried out if necessary (a rubbing method). The direction of the orientation regulation force can be controlled arbitrarily by selecting the direction for rubbing.

A method of providing orientation regulation force by rubbing method may be a method for bringing an orientational polymer film, which is formed on a surface of a substrate by applying a orientational polymer composition to the substrate and annealing the orientational polymer composition, into contact with a rotating rubbing roll on which a rubbing cloth is wound.

A photo-orientation film is usually formed on a surface of a substrate by applying a composition containing a photo-reactive group-containing polymer or monomer together with a solvent to the substrate and irradiating the applied composition with light (preferably, polarized UV). The photo-orientation film is preferable since the direction of the orientation regulation force can be controlled arbitrarily by selecting the polarizing direction of light for irradiation. Hereinafter, a composition containing a photo-reactive group-containing polymer or monomer may be sometimes referred to as a photo-orientation film formation composition.

A photo-reactive group refers to a group producing liquid crystal orientation performance by light irradiation. Specifically, the photo-reactive group may be photo-reactive groups involved in orientation induction of molecules generated by light irradiation or in photo-reaction such as isomerization reaction, dimerization reaction, photo-crosslinking reaction, or photo-degradation reaction which originates the liquid crystal orientation performance. Especially, photo-reactive groups involved in dimerization reaction or photo-crosslinking reaction are preferable because they are excellent in orientation property. The photo-reactive group preferably has an unsaturated bond, particularly a double bond, and particularly preferably at least one bond selected from the group consisting of a carbon-carbon double bond (C=C bond), a carbon-nitrogen double bond (C=N bond), a nitrogen-nitrogen double bond (N=N bond) and a carbon-oxygen double bond (C=O bond).

The photo-reactive group having a C=C bond may be a vinyl group, a polyene group, a stilbene group, a stilbazole group, a stilbazolium group, a chalcone group and a cinnamoyl group. The photo-reactive group having a C=N bond may be groups having a structure of an aromatic Schiff base, an aromatic hydrazone, etc. The photo-reactive group having a N=N bond may be an azobenzene group, an azonaphthalene group, an aromatic heterocyclic azo group, a bisazo group, a formazan group and a group having a structure of azoxybenzene. The photo-reactive group having a C=O bond may be a benzophenone group, a coumarin group, an anthraquinone group and a maleimide group. These groups may have a substituent such as alkyl group, alkoxy group, aryl group, allyloxy group, cyano group, alkoxycarbonyl group, hydroxyl group, sulfonic acid group or halogenated alkyl group.

Especially, a photo-reactive group involved in photo-dimerization reaction is preferable, and a cinnamonyl group and a chalcone group are preferable from the viewpoint that the polarized light irradiation dose necessary for photo-orientation is relatively low and a photo-orientation film excellent in heat stability and stability with lapse of time is easy to be obtained. A polymer having a photo-reactive group is particularly preferably those having a cinnamonyl group which forms a cinnamic acid structure in a polymer side chain terminal.

The solvent to be contained in the photo-orientation film formation composition may be those which are the same as solvents contained in the orientational polymer composition, and the solvent may be selected properly depending on the solubility of the photo-reactive group-containing polymer or monomer.

The content of the photo-reactive group-containing polymer or monomer in the photo-orientation film formation composition may be properly adjusted depending on the kind of the polymer or monomer and the aimed thickness of the photo-orientation film; however, it is preferably at least 0.2% by mass and more preferably in a range of 0.3 to 10% by mass. The photo-orientation film formation composition may contain a polymer material such as polyvinyl alcohol or polyimide and a photosensitizer to an extent that the characteristics of the photo-orientation film are not significantly deteriorated.

A method for applying the photo-orientation film formation composition to a substrate may be the same as the method for applying the orientational polymer composition to a substrate. A method for removing the solvent from the applied photo-orientation film formation composition may be the same as, for example, the method for removing the solvent from the orientational polymer composition.

The manner of polarized light irradiation may be a manner of directly irradiating the photo-orientation film formation composition applied to a substrate with polarized UV after solvent removal, or a manner of irradiating a substrate with polarized light and thereby transmitting the polarized light. In particular, the polarized light is preferably substantially parallel light. The wavelength of the polarized light for irradiation preferably falls within a wavelength range in which the photo-reactive group of the photo-reactive group-containing polymer or monomer easily absorbs light energy. Specifically, UV (ultraviolet rays) falling within a wavelength range of 250 to 400 nm is particularly preferable. A light source to be used for polarized light irradiation may be a xenon lamp, a high pressure mercury lamp, a super-high pressure mercury lamp, a metal halide lamp, ultraviolet laser of KrF or ArF, etc. and a high pressure mercury lamp, a super-high pressure mercury lamp and a metal halide lamp are more preferable. These lamps are preferable since having high emission intensity of ultraviolet ray with a wavelength of 313 nm. Light from the light source may be radiated through a proper polarizer to carry out polarized UV irradiation. Usable polarizers are a polarizing filter, polarizing prisms of Glan-Thomson and Glan-Taylor, and a wire-grid type polarizer.

When rubbing or polarized light irradiation is carried out with masking, a plurality of regions (patterns) having different liquid crystal orientation directions can be also formed.

A groove-orientation film is a film provided with liquid crystal orientation by irregularity patterns or a plurality of grooves in the film surface. H. V. Kennel et al. has reported the fact that when liquid crystal molecules are arranged on a substrate having a plurality of linear grooves at equal intervals, liquid crystal molecules are oriented along the direction of the grooves (Physical Review A24 (5), p 2713, 1981).

A specific method for forming the groove-orientation film on a surface of a substrate may be a method for forming irregularity patterns by exposing a photosensitive polyimide surface to light through an exposure mask having periodic patterned slits and thereafter removing the unnecessary polyimide film by development and rinsing treatment; a method including forming a UV-curable resin layer on a plate-like original disk having grooves on its surface, transferring the resin layer to a substrate film, followed by curing the resin layer; a method including transporting a substrate film on which a UV-curable resin layer is formed, pushing a roll-like original disk having a plurality of grooves against a surface of the UV-curable resin layer to form irregularities, followed by curing the resin layer; etc. The methods disclosed in JP-A-6-34976 and JP-A-2011-242743 may be employed.

Among these methods, preferred is a method including pushing a roll-like original disk having a plurality of grooves against a surface of the UV-curable resin layer to form irregularities, followed by curing the resin layer. In terms of durability, stainless (SUS) steel can be used as the roll-like original disk.

As the UV-curable resin, a polymer of monofunctional acrylate, a polymer of polyfunctional acrylate, and a polymer of their mixture may be used.

A monofunctional acrylate is a compound having one group selected from the group consisting of an acryloyloxy group (CH2=CH—COO—) and a methacryloyloxy group (CH2=C(CH3)—COO—) in a molecule. Hereinafter, an acryloyloxy group and a methacryloyloxy group may be sometimes referred to as a (meth)acryloyloxy group.

The monofunctional acrylate having one (meth)acryloyloxy group may be an alkyl (meth)acrylate having 4 to 16 carbon atoms, a β-carboxyalkyl (meth)acrylate having 2 to 14 carbon atoms, an alkylated phenyl (meth)acrylate having 2 to 14 carbon atoms, methoxy polyethylene glycol (meth) acrylate, phenoxy polyethylene glycol (meth)acrylate, isobornyl (meth)acrylate, etc.

A polyfunctional acrylate is a compound having two to six (meth)acryloyloxy groups in a molecule.

Examples of a bifunctional acrylate having two (meth) acryloyloxy groups may include 1,3-butanediol di(meth) acrylate; 1,6-hexanediol di(meth)acrylate; ethylene glycol di(meth)acrylate; diethylene glycol di(meth)acrylate; neopentyl glycol di(meth)acrylate; triethylene glycol di(meth) acrylate; tetraethylene glycol di(meth)acrylate; polyethylene glycol diacrylate; bisphenol A bis(acryloyloxyethyl) ether; ethoxylated bisphenol A di(meth)acrylate; propoxylated neopentyl glycol di(meth)acrylate; ethoxylated neopentyl glycol di(meth)acrylate, 3-methyl pentanediol di(meth)acrylate, etc.

A polyfunctional acrylate having three to six (meth) acryloyloxy groups may be:

trimethylolpropane tri(meth)acrylate; pentaerythritol tri (meth)acrylate; tris(2-hydroxyethyl) isocyanurate tri(meth) acrylate; ethoxylated trimethylolpropane tri(meth)acrylate; propoxylated trimethylolpropane tri(meth)acrylate; pentaerythritol tetra(meth)acrylate; dipentaerythritol penta(meth)acrylate; dipentaerythritol hexa(meth)acrylate; tripentaerythritol tetra(meth)acrylate; tripentaerythritol penta (meth)acrylate; tripentaerythritol hexa(meth)acrylate; tripentaerythritol hepta(meth)acrylate; tripentaerythritol octa(meth)acrylate;

a reaction product of pentaerythritol tri(meth)acrylate and an acid anhydride; a reaction product of dipentaerythritol penta(meth)acrylate and an acid anhydride; a reaction product of tripentaerythritol hepta(meth)acrylate and an acid anhydride;

caprolactone-modified trimethylolpropane tri(meth)acrylate; caprolactone-modified pentaerythritol tri(meth)acrylate; caprolactone-modified tris(2-hydroxyethyl) isocyanurate tri(meth)acrylate; caprolactone-modified pentaerythritol tetra(meth)acrylate; caprolactone-modified dipentaerythritol penta(meth)acrylate; caprolactone-modified dipentaerythritol hexa(meth)acrylate; caprolactone-modified tripentaerythritol tetra(meth)acrylate; caprolactone-modified tripentaerythritol penta(meth)acrylate; caprolactone-modified tripentaerythritol hexa(meth)acrylate; caprolactone-modified tripentaerythritol hepta(meth)acrylate; caprolactone-modified tripentaerythritol octa(meth)acrylate;

a reaction product of caprolactone-modified pentaerythritol tri(meth)acrylate and an acid anhydride; a reaction product of caprolactone-modified dipentaerythritol penta (meth)acrylate and an acid anhydride; a reaction product of caprolactone-modified tripentaerythritol hepta(meth)acrylate and an acid anhydride; etc. It is to be noted that (meth)acrylate mentioned herein as specific examples of a polyfunctional acrylate means an acrylate or a methacrylate. Further, the term "caprolactone-modified" means that ring-opened caprolactone or ring-opened polymer of caprolactone is introduced between an alcohol-derived portion of a (meth)acrylate compound and a (meth)acryloyloxy group.

Commercialized products may be used as the polyfunctional acrylate. The commercialized products may be A-DOD-N, A-HD-N, A-NOD-N, APG-100, APG-200, APG-400, A-GLY-9E, A-GLY-20E, A-TMM-3, A-TMPT, AD-TMP, ATM-35E, A-TMMT, A-9550, A-DPH, HD-N, NOD-N, NPG and TMPT (manufactured by Shin-Nakamura Chemical Co., Ltd.), "ARONIX M-220", "ARONIX M-325", "ARONIX M-240", "ARONIX M-270", "ARONIX M-309", "ARONIX M-310", "ARONIX M-321", "ARONIX M-350", "ARONIX M-360", "ARONIX M-305", "ARONIX M-306", "ARONIX M-450", "ARONIX M-451", "ARONIX M-408", "ARONIX M-400", "ARONIX M-402", "ARONIX M-403", "ARONIX M-404", "ARONIX M-405", and "ARONIX M-406" (manufactured by Toagosei Co., Ltd.), "EBECRYL 11", "EBECRYL 145", "EBECRYL 150", "EBECRYL 40", "EBECRYL 140", "EBECRYL 180", DPGDA, HDDA, TPGDA, HPNDA, PETIA, PETRA, TMPTA, TMPEOTA, DPHA, EBECRYL series (manufactured by Daicel-Cytec Co., Ltd.), etc.

In the irregularities of the groove-orientation film, the width of a projection is preferably 0.05 to 5 μm, the width of a recess is preferably 0.1 to 5 μm, the difference between a projection and a recess is 2 μm or less, preferably 0.01 to 1 μm or less. If is the difference falls within the range, it is possible to obtain liquid crystal orientation with little orientation disorder.

The thickness of the orientation film is usually 10 nm to 10000 nm, preferably 10 nm to 1000 nm, and more preferably 10 nm to 500 nm.

A method for applying the present composition may be the same as those described as examples of the method for applying the orientational polymer composition to a substrate.

<Step (2)>

When the present composition contains a solvent, usually, the solvent is removed from the applied present composition. A method for removing the solvent may be a natural drying method, a blow drying method, heat drying, a vacuum drying method, etc.

The polymerizable liquid crystal compound contained in the applied present composition is usually heated to a temperature for transition to a solution state and thereafter cooled to a temperature for liquid crystal orientation to form an oriented liquid crystal phase.

The temperature for orienting the polymerizable liquid crystal compound contained in the applied present composition may be determined by previously observing the texture using a composition containing the polymerizable liquid crystal compound. The solvent removal and the liquid crystal orientation may be carried out simultaneously. The temperature at that time is preferably 50 to 200° C. although depending on the kind of the solvent to be removed and the kind of the polymerizable liquid crystal compound, and more preferably in a range of 80 to 130° C. when the substrate is a resin substrate.

When a ¼ wavelength plate is used as a substrate to obtain a circularly polarizing plate having the present polarizing film and the ¼ wavelength plate, the orientation direction of the polymerizable liquid crystal compound may be controlled to form substantially 45° between the transmission axis of a polarizing film to be obtained and the slow axis (optical axis) of the ¼ wavelength plate.

<Step (3)>

The polymerizable liquid crystal compound is polymerized by irradiating the oriented polymerizable liquid crystal compound with active energy.

A polarizing film is obtained which contains the polymerizable liquid crystal compound polymerized in an oriented state by polymerizing the oriented polymerizable liquid crystal compound, and the compound (1) oriented together with the polymerizable liquid crystal compound.

A polarizing film containing the polymerizable liquid crystal compound polymerized with retaining a smectic liquid crystal phase has high polarizing performance as compared with a conventional host-guest type polarizing film, that is, a polarizing film obtained by polymerizing a polymerizable liquid crystal compound or the like with retaining a nematic liquid crystal phase, and is also excellent in polarizing performance and strength as compared with a polarizing film obtained by applying only a dichroic dye or a lyotropic liquid crystal-type liquid crystal compound.

A light source for the active energy beam may be those which can emit ultraviolet rays, electron beam, x-ray, etc., and preferably a light source such as low pressure mercury lamp, medium pressure mercury lamp, high pressure mercury lamp, super-high pressure mercury lamp, chemical lamp, black light lamp or microwave excitation mercury lamp, which has light emission distribution in a wavelength of 400 nm or less.

The irradiation energy of the active energy beam is set in such a way that a wavelength region effective to activate a polymerization initiator has a radiation intensity of 10 to 5000 mJ/cm$^2$, and more preferably 100 to 2000 mJ/cm$^2$. If the irradiation energy is lower than 10 mJ/cm$^2$, the polymerizable liquid crystal compound tends to be insufficiently cured.

The thickness of the present polarizing film thus formed is preferably in a range of 0.5 µm or more and 10 µm or less, and more preferably 1 µm or more and 5 µm or less. The thickness of the present polarizing film can be measured by an interference thickness meter, a laser microscope or a contact type thickness meter.

The present polarizing film is particularly preferable if it has a Bragg peak in an x-ray diffraction measurement. The present polarizing film having such a Bragg peak may be those which show diffraction peaks derived from, for example, a hexatic phase and a crystal phase.

The local maximum absorption ($\lambda$max1) of the present polarizing film exists preferably in a range of 400 to 550 nm, more preferably in a range of 410 to 540 nm, and furthermore preferably in a range of 430 to 530 nm. Further, it is preferable that the $\lambda$max1 is shifted to longer wavelength as compared with the local maximum absorption ($\lambda$max2) measured by dissolving the compound (1) contained in the present polarizing film in a proper solvent. Shift to longer wavelength is exhibited when the compound (1) is dispersed among molecular chains formed by the polymerized polymerizable liquid crystal compound and shows strong interaction of the compound (1) to the molecular chains. The term "shift to longer wavelength" means that the difference of the local maximum absorption ($\lambda$max1-$\lambda$max2) becomes a positive value, and the difference is preferably 15 nm or more and more preferably 30 nm or more.

The dichroic ratio of the present polarizing film is preferably 15 or higher and more preferably 25 or higher.

If a substrate used is not a ¼ wavelength plate, a circularly polarizing plate can be obtained by laminating the obtained present polarizing film and a ¼ wavelength plate. In this case, it is preferable to carry out the lamination in such a manner that the angle between the transmission axis of the present polarizing film and the slow axis (optical axis) of the ¼ wavelength plate becomes substantially 45°. It is also possible to obtain a polarizing plate having a function as an optical compensation film by making the transmission axis of the present polarizing film and the optical axis of a retardation film such as ¼ wavelength plate coincident with each other or orthogonal to each other.

The present polarizing film and the ¼ wavelength plate may be laminated by using a substrate on which the present polarizing film is formed or a substrate on which the orientation film is formed, or may be laminated after removing either a substrate or a substrate together with the orientation film. The present polarizing film formed on a surface of a substrate or on a surface of a substrate on which the orientation film is formed and the ¼ wavelength plate may be laminated by, for example, sticking the surface of the substrate on which the present polarizing film is formed and the ¼ wavelength plate with an adhesive, and thereafter removing the substrate or the substrate on which the orientation film is formed. In this case, the adhesive may be applied to the present polarizing film or to the ¼ wavelength plate.

<Continuous Production Method for Polarizing Film>

Preferably, the present polarizing plate is continuously produced in a Roll to Roll manner. One example of a main part of a continuous production method in a Roll to Roll manner will be described with reference to FIG. 1.

A first roll 210 having a first roll core 210A on which a substrate is wound is easily available in markets. A substrate in the form of a roll and available in markets may be films of cellulose ester, cyclic olefin-based resin, polycarbonate, polyethylene terephthalate and polymethacrylic acid ester among the examples for the substrate described above.

Successively, the substrate is wound off from the first roll 210. A method for winding off the substrate is carried out by installing proper rotating means in the roll core 210A of the first roll 210 and rotating the first roll 210 by the rotating means. The method may be also carried out by installing a proper auxiliary roll 300 in the substrate transportation direction from the first roll 210 and winding off the substrate by rotating means of the auxiliary roll 300. Further, the method may be also carried out by installing rotating means in both of the first roll core 210A and the auxiliary roll 300 and winding off the substrate while applying proper tensile force to the substrate.

A photo-orientation film formation composition is applied to a surface of the substrate wound off from the first roll 210 by an application apparatus 211A when the substrate passes through the application apparatus 211A. The application apparatus 211A for continuously applying the photo-orientation film formation composition is preferably an apparatus for a gravure coating method, a die coating method and a flexographic method.

The substrate passed through the application apparatus 211A is transported to a drying furnace 212A and dried in the drying furnace 212A so that a first coating film is continuously formed on the substrate surface. For example, a hot air blowing-type drying furnace in which a blowing drying method and a heat drying method are combined may be used for the drying furnace 212A. The temperature of the drying furnace 212A is set depending on the kind of the solvent contained in the photo-orientation film formation composition, etc. The drying furnace 212A may be composed of a plurality of zones each having different temperature or a plurality of drying furnaces each having different temperature and arranged in series.

The obtained first coating film is irradiated with polarized light by a polarizing UV irradiation apparatus 213A to obtain a photo-orientation film.

Successively, the substrate on which the photo-orientation film is formed passes through an application apparatus 211B. After the present composition containing the solvent is applied onto the photo-orientation film by the application apparatus 211B, the substrate passes through a drying furnace 212B so that a second coating film is formed in which the polymerizable liquid crystal compound contained in the present composition is oriented. The drying furnace 212B plays a role for removing the solvent from the solvent-containing present composition applied onto the photo-orientation film and also a role for providing heat energy to orient the polymerizable liquid crystal compound contained in the present composition. Similarly to the drying furnace 212A, the drying furnace 212B may be composed of a plurality of zones each having different temperature or a plurality of drying furnaces each having different temperature and arranged in series.

The substrate is transported to an active energy beam irradiation apparatus 213B in a state where the polymerizable liquid crystal compound contained in the second coating film is oriented. In the active energy beam irradiation apparatus 213B, irradiation with active energy beam is further carried out. The polymerizable liquid crystal compound is polymerized in an oriented state by irradiation with active energy beam through the active energy beam irradiation apparatus 213B so that a polarizing film is obtained.

Consequently, the present polarizing plate produced in a continuous manner is wound around a second roll core 220A to be in the form of a second roll 220. The winding together with a proper spacer may be carried out.

The present polarizing plate can be produced continuously in a Roll-to-Roll manner by passing the substrate through the application apparatus 211A, the drying furnace 212A, the polarized UV irradiation apparatus 213A, the application apparatus 211B, the drying furnace 212B, and the active energy beam irradiation apparatus 213B in this order from the first roll 210 as described above.

In the production method depicted in FIG. 1, the method for continuously producing the present polarizing film is described, but it is also possible to produce the present polarizing film by, for example, passing the substrate through the application apparatus 211A, the drying furnace 212A and the polarized UV irradiation apparatus 213A in this order from the first roll; winding the resulting substrate around a roll core so that a rolled laminate body of the substrate and the photo-orientation film is produced; and successively winding off the rolled laminate body and passing the laminate body through the application apparatus 211B, the drying furnace 212B, and the active energy beam irradiation apparatus 213B in this order.

When the present polarizing film is produced in the form of the second roll 220, the long-sized present polarizing film is wound off from the second roll 220 and cut into a prescribed size. The cut polarizing film may be stuck to a ¼ wavelength plate to produce a circularly polarizing plate. It is also possible to continuously produce a long-sized circularly polarizing film by preparing a third roll having a roll core on which a long ¼ wavelength plate is wound.

Figure 2:
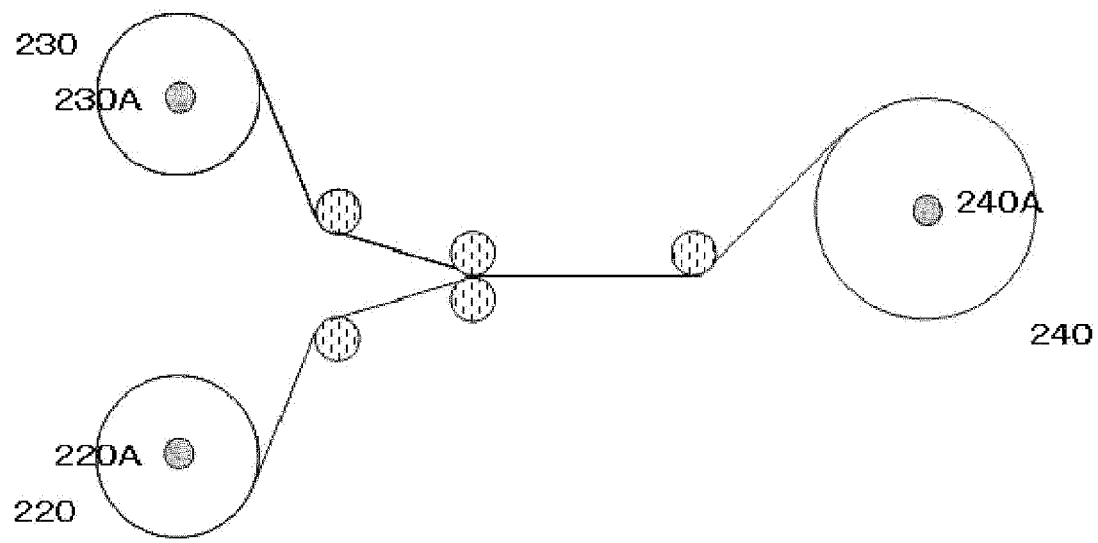
FIG. 2 is a schematic diagram illustrating a continuous production method for a circularly polarizing plate having the polarizing film of the present invention.

A method for continuously producing a long-sized circularly polarizing plate will be described with reference to FIG. 2. The production method includes the steps of:

continuously winding off the present polarizing film from the second roll 220 and continuously winding off a long-sized ¼ wavelength plate from a third roll 230 on which the long-sized ¼ wavelength plate is wound;

continuously sticking the present polarizing film and the long-sized ¼ wavelength plate to obtain a long-sized circularly polarizing plate; and winding the obtained long-sized circularly polarizing plate around a fourth roll core 240A to obtain a fourth roll 240. This method is so-called roll to roll adhesion. An adhesive may be used for the adhesion.

<Use of Present Polarizing Film>

The present polarizing film, the polarizing film containing the compound (1), and the circularly polarizing plate having the present polarizing film and the ¼ wavelength plate can be used for various kinds of display devices.

A display device is a device having a display element and has a light emitting element or a light emitting device as a light emitting source. Examples of a display device equipped with the present polarizing plate may include a liquid crystal display device, an organic electroluminescence (EL) display device, an inorganic electroluminescence (EL) display device, an electron emission display device (e.g., field emission display device (FED), surface emission display device (SED)), electronic paper (display device using electronic ink or electrophoresis element), a plasma display device, a projection type display device (e.g., grating light valve (GLV) display device, display device having a digital micro-mirror device), a piezoelectric ceramic display, etc. The liquid crystal display device includes all of a transmission type liquid crystal display device, a semi-transmission type liquid crystal display device, a reflection type liquid crystal display device, a direct viewing type liquid crystal display device and a projection type liquid crystal display device. These display devices may be display devices for displaying two-dimensional images or stereoscopic display devices for displaying three-dimensional images.

The polarizing film is particularly effectively usable for a liquid crystal display device, an organic electroluminescence (EL) display device, and an inorganic electroluminescence (EL) display device.

The circularly polarizing plate having the present polarizing film and the ¼ wavelength plate is particularly effectively usable for an organic electroluminescence (EL) display device and an inorganic electroluminescence (EL) display device.

When the present polarizing film is used for a liquid crystal display device, the present polarizing film may be arranged outside of a liquid crystal cell or may be arranged inside of a liquid crystal cell.

Figure 3:
FIG. 3 is a schematic diagram of a liquid crystal cell having the polarizing film of the present invention.

Hereinafter, a first configuration in the case where the polarizing film is arranged particularly inside of the liquid crystal cell of a transmission-type active matrix color liquid crystal display device will be described with reference to FIG. 3. A display device 30 includes a first substrate 31, a first present polarizing film 32, a color filter layer 33, a leveling layer 34, an ITO electrode layer 35, a first orientation film 36, a liquid crystal layer 37, a second orientation film 38, a second present polarizing film 39, a TFT layer 40 having a thin film transistor circuit and a pixel electrode, and a second substrate 41.

The color filter layer is a layer for taking out light with a desired wavelength from light incident from the substrate 41 side and may be a layer which absorbs light with a wavelength other than a desired wavelength from white light and transmits only the light with a desired wavelength or a layer which converts the wavelength of incident light and emits the light with a desired wavelength.

Each of the first and second present polarizing films may contain an orientation film in the first and second substrate sides. The orientation film may be a rubbing orientation film or a photo-orientation film. The first present polarizing film may contain a retardation layer.

Figure 4:
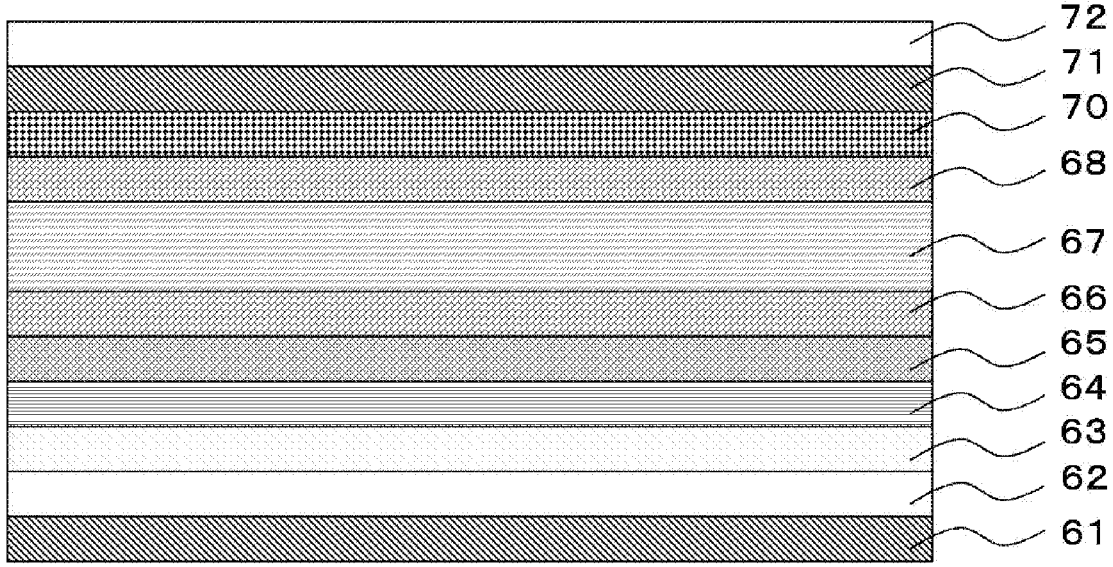
FIG. 4 is a schematic diagram of the liquid crystal cell having the polarizing film of the present invention.

Hereinafter, a second configuration will be described with reference to FIG. 4. A display device 60 includes a first substrate 61, a first present polarizing film 62, a color filter layer 63, a leveling layer 64, an ITO electrode layer 65, a first orientation film 66, a liquid crystal layer 67, a second orientation film 68, a TFT layer 70 having a thin film transistor circuit and a pixel electrode, a second substrate 71, and a second polarizing film 72.

The second polarizing film 72 arranged on the opposite side to the TFT layer 70 of the second substrate 71 may be the polarizing film of the present invention or may be a polarizing film produced by dyeing polyvinyl alcohol with iodine, followed by stretching.

Figure 5:
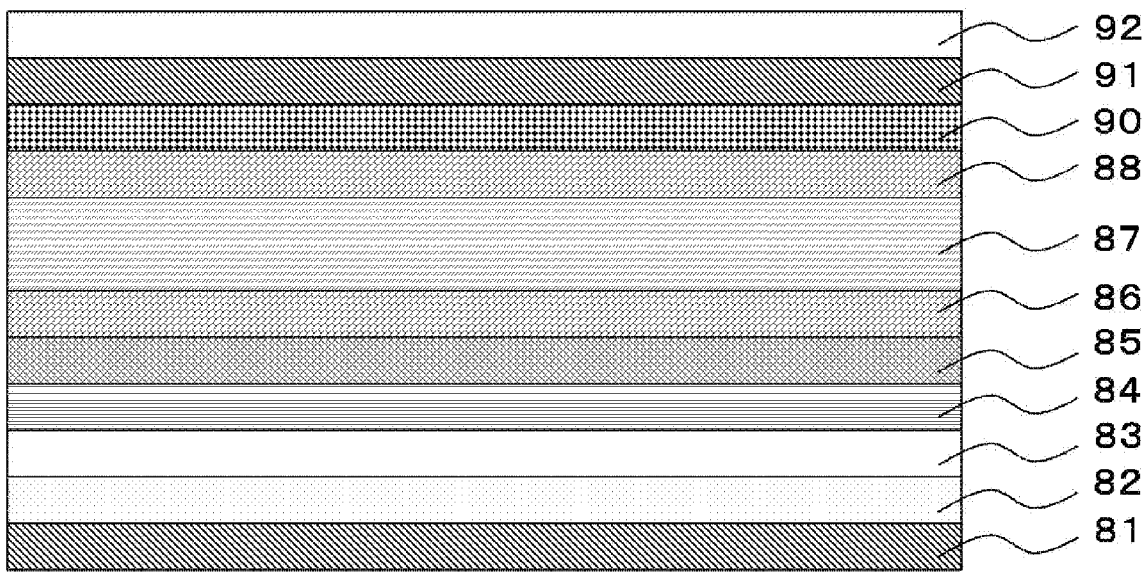
FIG. 5 is a schematic diagram of the liquid crystal cell having the polarizing film of the present invention.

Hereinafter, a third configuration will be described with reference to FIG. 5. A display device 80 includes a first substrate 81, a color filter layer 82, a first present polarizing film 83, a leveling layer 84, an ITO electrode layer 85, a first orientation film 86, a liquid crystal layer 87, a second orientation film 88, a TFT layer 90 having a thin film transistor circuit and a pixel electrode, a second substrate 91, and a second polarizing film 92.

In the third configuration, the second polarizing film 92 may be the polarizing film of the present invention or may be a polarizing film produced by dyeing polyvinyl alcohol with iodine, followed by stretching. When the second polarizing film 92 is the polarizing film of the present invention, the second polarizing film may be disposed between the second substrate 91 and the TFT layer 90 similarly to the first configuration.

The color filter layer 82 in the third configuration may be arranged on the side of the first substrate 81 opposite to the liquid crystal layer.

Polarized light may be diffused by particles contained in the color filter layer to possibly cancel polarization. For this reason, the third configuration in which the first polarizing film according to the present invention is arranged in the liquid crystal layer side rather than in the color filter layer side is preferable among the first to the third configurations.

EXAMPLES

Hereinafter, the present invention will be described further in detail with reference to examples. In the examples, "%" and "part(s)" mean % by mass and parts by mass unless otherwise specified.

Example 1

Production of Compound (1) (Compound Represented by the Following Formula (1A) [Compound (1A)])

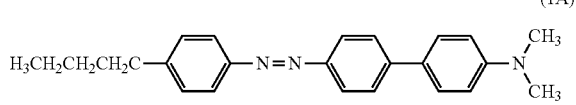

(1A)

A compound (1A) was synthesized according to the following scheme.

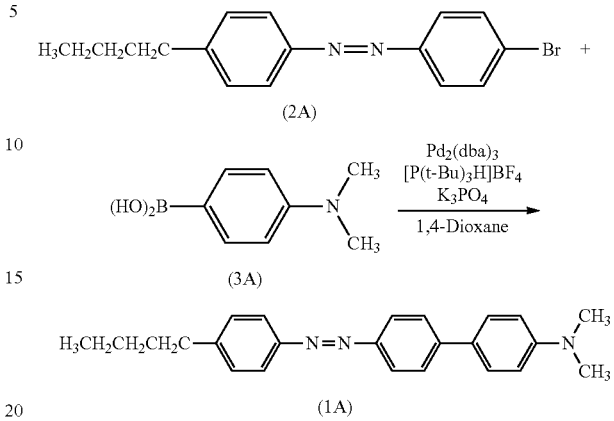

First, 0.15 g of a compound represented by the formula (2A) [compound (2A)], 0.090 g of a compound represented by the formula (3A) [compound (3A)], 0.50 g of potassium phosphate ($K_3PO_4$), 0.0087 g of tris(dibenzylideneacetone)dipalladium(0), 0.011 g of tri-tert-butylphosphonium tetrafluoroborate, and 3 g of 1,4-dioxane were mixed and stirred at 100° C. for 18 hours under nitrogen atmosphere. The obtained mixed solution was concentrated to remove 1,4-dioxane by distillation, and thereafter refined by silica gel column chromatography (eluent: toluene) and concentrated to remove toluene by distillation. The obtained solid was washed with acetonitrile and thereafter vacuum dried to obtain 0.10 g of a compound (1A), an orange solid. The yield was 59% on the basis of the compound (2A). Spectral data Mw: 357 (GC-MS), maximum absorption wavelength (λmax2)=394 nm (chloroform solution).

The compound (2A) was synthesized according to the following scheme.

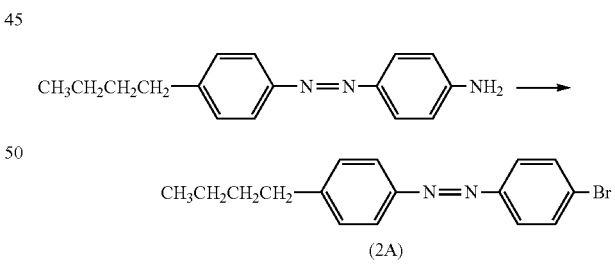

A mixture containing 3.0 g of 4-n-butyl-4'-aminoazobenzene and 15 g of water was cooled to 0° C., and 4.0 g of 48% hydrobromic acid and 4.9 g of an aqueous 33% sodium nitrite solution were dropwise added. The obtained mixture was dropwise added at 60° C. to a mixture containing 3.4 g of cupper (I) bromide and 17 g of 48% hydrobromic acid and the resultant was kept at 60° C. for 1 hour. After the resultant was cooled to 25° C., a precipitate was collected by filtration to obtain 1.6 g of a compound represented by the formula (2A) (hereinafter, referred to as compound (2A)).

Example 2

Production of Compound (1) (Compound Represented by the Following Formula (1B) [Compound (1B)])

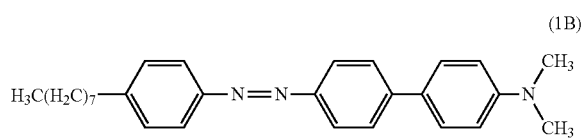

A compound (1B) was synthesized according to the following scheme.

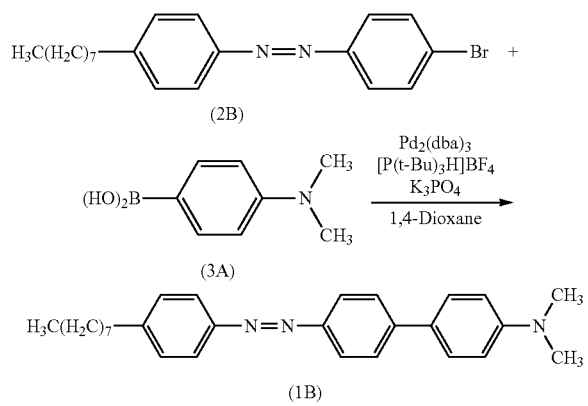

First, 0.12 g of a compound represented by the formula (2B) [compound (2B)], 0.064 g of a compound represented by the formula (3A) [compound (3A)], 0.34 g of potassium phosphate ($K_3PO_4$), 0.0059 g of tris(dibenzylideneacetone) dipalladium(0), 0.0075 g of tri-tert-butylphosphonium tetrafluoroborate, and 2.4 g of 1,4-dioxane were mixed and stirred at 100° C. for 18 hours under nitrogen atmosphere. The obtained mixed solution was concentrated to remove 1,4-dioxane by distillation, and thereafter refined by silica gel column chromatography (eluent: toluene) and concentrated to remove toluene by distillation. The obtained solid was washed with acetonitrile and thereafter vacuum dried to obtain 0.067 g of a compound (1B), an orange solid. The yield was 52% on the basis of the compound (2B). Spectral data Mw: 413 (GC-MS), λmax2=398 nm (chloroform solution).

Example 3

Production of Compound (1) (Compound Represented by the Following Formula (1C) [Compound (1C)])

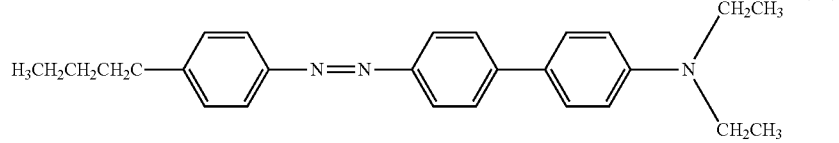

A compound (1C) was synthesized according to the following scheme.

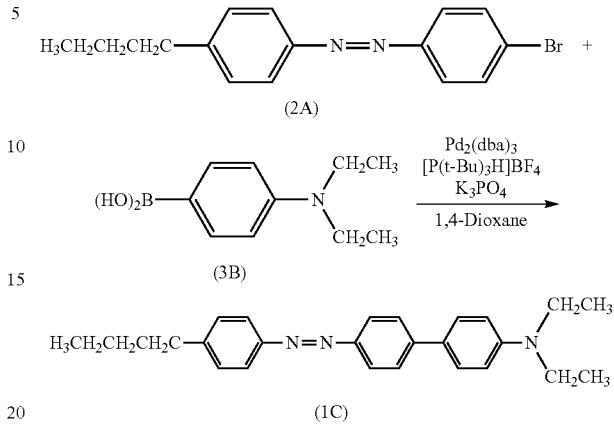

First, 0.12 g of a compound represented by the formula (2A) [compound (2A)], 0.088 g of a compound represented by the formula (3B) [compound (3B)], 0.40 g of potassium phosphate ($K_3PO_4$), 0.0069 g of tris(dibenzylideneacetone) dipalladium(0), 0.0088 g of tri-tert-butylphosphonium tetrafluoroborate, and 2.4 g of 1,4-dioxane were mixed and stirred at 100° C. for 18 hours under nitrogen atmosphere. The obtained mixed solution was concentrated to remove 1,4-dioxane by distillation, and thereafter refined by silica gel column chromatography (eluent: chloroform/heptane=⅓) and concentrated to remove the solvents by distillation. The obtained solid was washed with acetonitrile and thereafter vacuum dried to obtain 0.054 g of a compound (1C), an orange solid. The yield was 36% on the basis of the compound (2A). Spectral data Mw: 385 (GC-MS), λmax2=418 nm (chloroform solution).

Example 4

Production of Compound (1) (Compound Represented by the Following Formula (1D) [Compound (1D)])

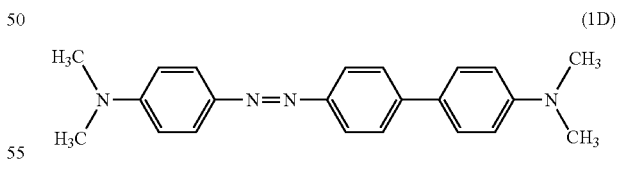

A compound (1D) was synthesized according to the following scheme.

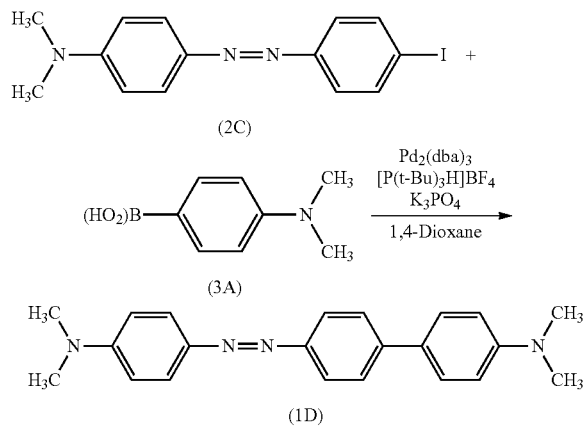

First, 0.15 g of a compound represented by the formula (2C) [compound (2C)], 0.078 g of a compound represented by the formula (3A) [compound (3A)], 0.45 g of potassium phosphate ($K_3PO_4$), 0.0078 g of tris(dibenzylideneacetone)dipalladium(0), 0.0099 g of tri-tert-butylphosphonium tetrafluoroborate, and 3 g of 1,4-dioxane were mixed and stirred at 100° C. for 18 hours under nitrogen atmosphere. The obtained mixed solution was concentrated to remove 1,4-dioxane by distillation, and thereafter refined by silica gel column chromatography (eluent: chloroform) and concentrated to remove chloroform by distillation. The obtained solid was washed with acetonitrile and thereafter vacuum dried to obtain 0.090 g of a compound (1D), an orange solid. The yield was 60% on the basis of the compound (2C). Spectral data Mw: 344 (GC-MS), λmax2=436 nm (chloroform solution).

Example 5

Production of Compound (1) (Compound Represented by the Following Formula (1E) [Compound (1E)])

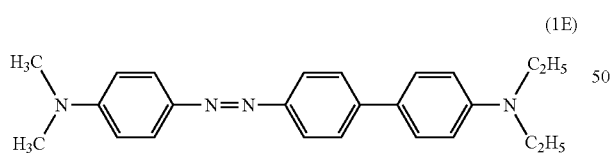

A compound (1E) was synthesized according to the following scheme.

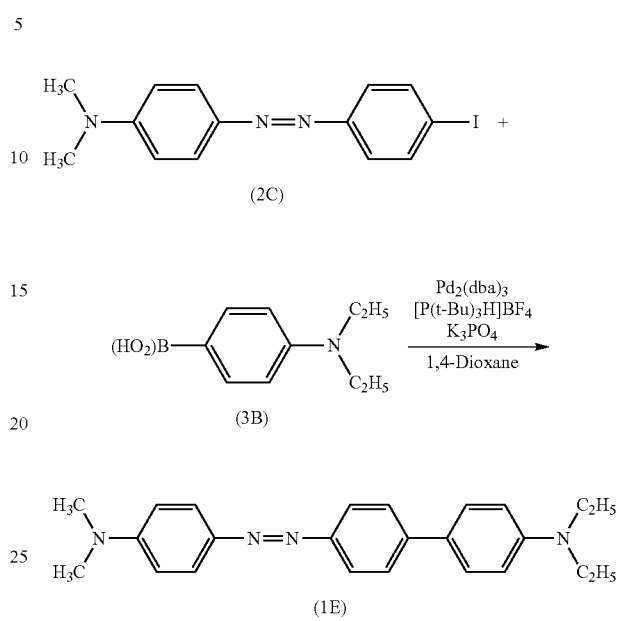

First, 0.20 g of a compound represented by the formula (2C) [compound (2C)], 0.132 g of a compound represented by the formula (3B) [compound (3B)], 0.60 g of potassium phosphate ($K_3PO_4$), 0.0104 g of tris(dibenzylideneacetone)dipalladium(0), 0.0132 g of tri-tert-butylphosphonium tetrafluoroborate, and 4 g of 1,4-dioxane were mixed and stirred at 100° C. for 18 hours under nitrogen atmosphere. The obtained mixed solution was concentrated to remove 1,4-dioxane by distillation, and thereafter refined by silica gel column chromatography (eluent: chloroform) and concentrated to remove chloroform by distillation. The obtained solid was washed with acetonitrile and thereafter vacuum dried to obtain 0.187 g of a compound (1E), an orange solid. The yield was 89% on the basis of the compound (2C). Spectral data Mw: 372 (GC-MS), λmax2=442 nm (chloroform solution).

Example 6

Production of Compound (1) (Compound Represented by the Following Formula (1F) [Compound (1F)])

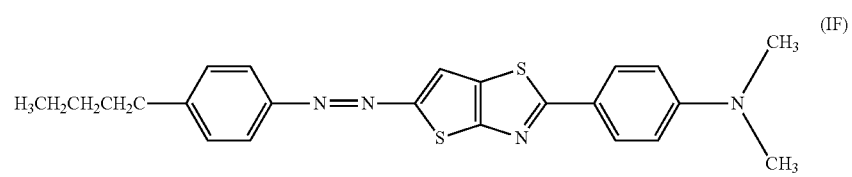

A compound (1F) was synthesized according to the following scheme.

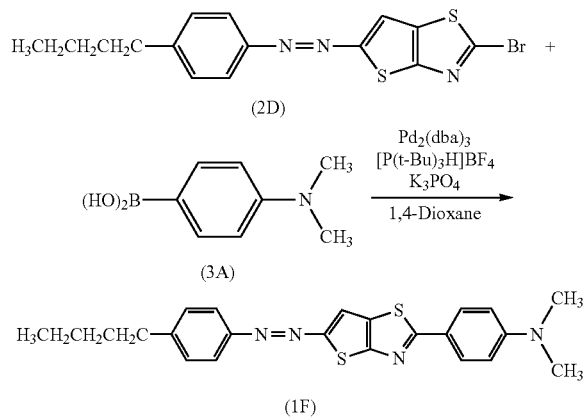

First, 0.20 g of a compound represented by the formula (2D) [compound (2D)], 0.104 g of a compound represented by the formula (3A) [compound (3A)], 0.56 g of potassium phosphate ($K_3PO_4$), 0.0193 g of tris(dibenzylideneacetone)dipalladium(0), 0.0244 g of tri-tert-butylphosphonium tetrafluoroborate, and 4 g of 1,4-dioxane were mixed and stirred at 100° C. for 18 hours under nitrogen atmosphere. The obtained mixed solution was concentrated to remove 1,4-dioxane by distillation, and thereafter refined by silica gel column chromatography (eluent: chloroform/heptane=1/3) and concentrated to remove the solvents by distillation. The obtained solid was washed with acetonitrile and thereafter vacuum dried to obtain 0.035 g of a compound (1F), an orange solid. The yield was 16% on the basis of the compound (2D). M/Z: 420 (EI-MS), λmax2: 488 nm (chloroform solution).

Example 7

Production of Compound (1) (Compound Represented by the Following Formula (1G) [Compound (1G)])

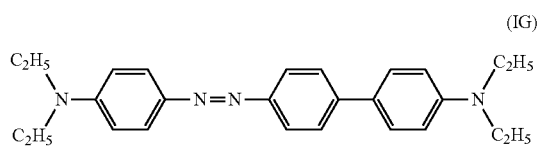

A compound (1G) was synthesized according to the following scheme.

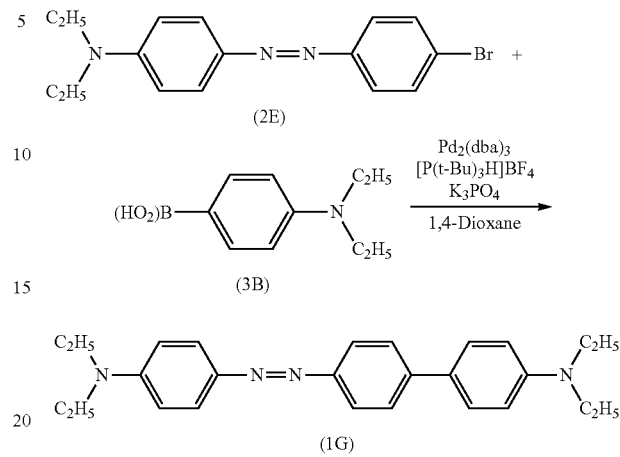

First, 0.15 g of a compound represented by the formula (2E) [compound (2E)], 0.11 g of a compound represented by the formula (3B) [compound (3B)], 0.48 g of potassium phosphate ($K_3PO_4$), 0.0083 g of tris(dibenzylideneacetone)dipalladium(0), 0.0105 g of tri-tert-butylphosphonium tetrafluoroborate, and 3 g of 1,4-dioxane were mixed and stirred at 100° C. for 18 hours under nitrogen atmosphere. The obtained mixed solution was concentrated to remove 1,4-dioxane by distillation, and thereafter refined by silica gel column chromatography (eluent: chloroform) and concentrated to remove chloroform by distillation. The obtained solid was washed with acetonitrile and thereafter vacuum dried to obtain 0.069 g of a compound (1E), an orange solid. The yield was 34% on the basis of the compound (2C). Spectral data M/Z: 400 (EI-MS), λmax2=456 nm (chloroform solution).

[Polymerizable Liquid Crystal Compound]

A compound represented by the following formula (4-6) [compound (4-6)], a compound represented by the following formula (4-8) [compound (4-8)], a compound represented by the following formula (4-22) [compound (4-22)], and a compound represented by the following formula (4-25) [compound (4-25)] were used as a polymerizable liquid crystal compound contained in the present composition.

The compound (4-6) was synthesized by the method described in Lub et al. Recl. Tray. Chim. Pays-Bas, 115, 321-328 (1996). The compound (4-8) was also produced in accordance with this method.

The compound (4-22) and the compound (4-25) were produced in accordance with the method disclosed in Japanese Patent No. 4719156.

Compound (4-6):

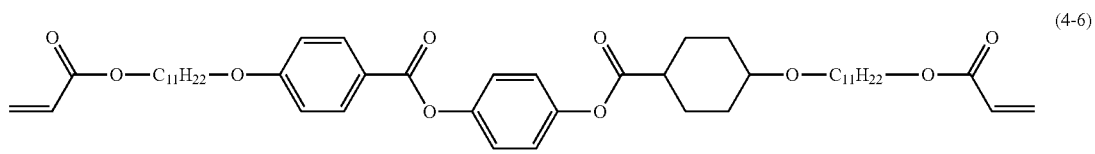

[Measurement of Phase Transition Temperature]

The phase transition temperature of the compound (4-6) was confirmed by measuring the phase transition temperature of a film composed of the compound (4-6). The process was as follows.

A film composed of the compound (4-6) was formed on a glass substrate on which an orientation film was formed, and while the film was heated, the phase transition temperature was confirmed by observing the texture with a polarizing microscope (BX-51, manufactured by Olympus Corporation). While being cooled after heated to 120° C., the compound (4-6) caused phase transition to a nematic phase at 112° C., to a smectic A phase at 110° C., and to a smectic B phase at 94° C.

Compound (4-8):

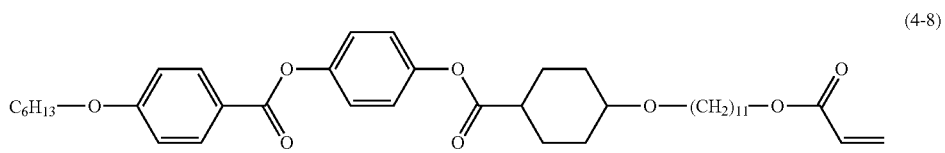

(4-8)

[Measurement of Phase Transition Temperature]

The phase transition temperature of the compound (4-8) was confirmed in the same manner as in the phase transition temperature measurement for the compound (4-6). While being cooled after heated to 140° C., the compound (4-8) caused phase transition to a nematic phase at 131° C., to a smectic A phase at 80° C., and to a smectic B phase at 68° C.

Compound (4-22):

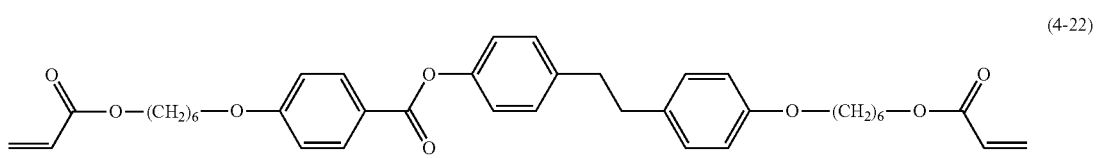

(4-22)

[Measurement of Phase Transition Temperature]

The phase transition temperature of the compound (4-22) was confirmed in the same manner as in the phase transition temperature measurement for the compound (4-6). While being cooled after heated to 140° C., the compound (4-22) caused phase transition to a nematic phase at 106° C., to a smectic A phase at 103° C., and to a smectic B phase at 86° C.

Compound (4-25):

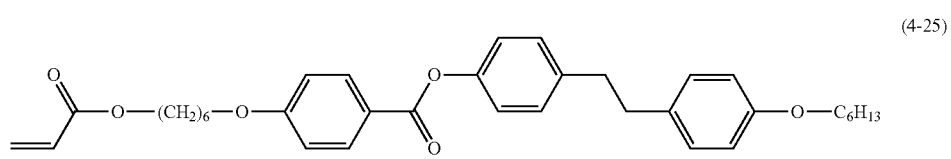

(4-25)

[Measurement of Phase Transition Temperature]

The phase transition temperature of the compound (4-25) was confirmed in the same manner as in the phase transition temperature measurement for the compound (4-6). While being cooled after heated to 140° C., the compound (4-25) caused phase transition to a nematic phase at 119° C., to a smectic A phase at 100° C., and to a smectic B phase at 77° C.

Example 8

Preparation of Composition

A composition (1) was obtained by mixing the following components and stirring the resulting mixture at 80° C. for 1 hour.

| Polymerizable liquid crystal compound: | |
| --- | --- |
| compound (4-6) | 75 parts |
| compound (4-8) | 25 parts |
| Compound (1): | |
| compound (1A) | 2.5 parts |
| Polymerization initiator: | |
| 2-dimethylamino-2-benzyl-1-(4-morpholinophenyl)butan-1-one (Irgacure 369: manufactured by Ciba Specialty Chemicals Inc.) | 6 parts |
| Leveling agent: | |
| polyacrylate compound (BYK-361N: manufactured by BYK-Chemie GmbH) | 1.5 parts |
| Solvent: | |
| Toluene | 250 parts |

[Measurement of Phase Transition Temperature]

The phase transition temperature of the components contained in the composition (1) was measured in the same manner as that for the compound (4-6). While being cooled after heated to 140° C., the components caused phase transition to a nematic phase at 115° C., to a smectic A phase at 105° C., and to a smectic B phase at 75° C.

[Production and Evaluation of Polarizing Film]

1. Formation of Orientation Film

An aqueous 2 mass % solution of polyvinyl alcohol (completely saponified-type polyvinyl alcohol 1000, manufactured Wako Pure Chemical Industries, Ltd.) was applied onto a glass substrate by spin coating method, and dried to form a film with a thickness of 100 nm. Successively, the surface of the obtained film was rubbed to form an orientation film. The rubbing treatment was carried out under conditions of a pushing depth of 0.15 mm, a rotation speed of 500 rpm, and 16.7 mm/s with a cloth (trade name: YA-20-RW, manufactured by Yoshikawa Chemical Co., Ltd.) using a semi-automatic rubbing apparatus (trade name: LQ-008 model, Joyo Engineering Co., Ltd.). A laminate body 1 having the orientation film formed on the glass substrate was obtained by the rubbing treatment.

2. Formation of Polarizing Film

The composition (1) was applied onto the orientation film of the laminated body 1 by spin coating method, and heated and dried on a hot plate at 120° C. for 1 minute and thereafter quickly cooled to room temperature to form a dried coating film containing a polymerizable liquid crystal compound oriented on the orientation film. Next, the dried coating film was irradiated with ultraviolet rays at an exposure dose of 2000 mJ/cm$^2$ (based on 365 nm) using a UV irradiation apparatus (SPOT CURE SP-7; USHIO Inc.) to polymerize the polymerizable liquid crystal compound contained in the dried coating film while retaining the orientation state, so that a polarizing film (1) was formed from the dried coating film and thus a laminated body 2 was obtained. When the thickness of the polarizing film was measured by a laser microscope (OLS 3000, manufactured by Olympus Corporation), it was 1.7 μm.

3. X-Ray Diffraction Measurement

X-ray diffraction measurement for the polarizing film (1) was carried out using an x-ray diffraction apparatus X'Pert PRO MPD (manufactured by Spectris Co., Ltd.). Using Cu as a target, x-rays generated under conditions of an x-ray tube current of 40 mA and an x-ray tube pressure of 45 kV were incident from the rubbing direction (the rubbing direction of the orientation film formed under the polarizing film is determined in advance) through a stationary emission slit ½°, and scanning was carried out at a scanning step 2θ=0.01671° in a scanning range 2θ=4.0 to 40.0° to obtain a sharp diffraction peak (Bragg peak) with a half peak width (FWHM)=about 0.31° around 2θ=20.1°. The same result was obtained in the case of incidence from the perpendicular direction to rubbing. The periodic order (d) calculated from the peak position was about 4.4 angstroms and it was found that the polarizing film (1) had a structure corresponding to a higher-order smectic phase.

4. Dichroic Ratio Measurement

The absorbance ($A^1$) in the transmission axis direction and the absorbance ($A^2$) in the absorption axis direction at the local maximum absorption wavelength were measured by double beam method using an apparatus including a spectrophotometer (UV-3150, manufactured by Shimadzu Corporation) and a folder equipped with the laminate body 2 therein. In the reference side of the folder, a mesh for cutting 50% of light quantity was installed. The ratio ($A^2/A^1$) was calculated from the measured absorbance ($A^1$) in the transmission axis direction and the measured absorbance ($A^2$) in the absorption axis direction as a dichroic ratio. The local maximum absorption wavelength (λmax1) was 440 nm and the dichroic ratio at the wavelength was as high as 36. It can be said that as the dichroic ratio is higher, the polarizing film is more useful. The local maximum absorption wavelength (λmax2) of the compound (1A) used for the composition (1), which was measured in a solution state (chloroform solution), was 394 nm. It was found that the local maximum absorption wavelength was shifted toward a longer side in wavelength. The shift toward a longer side in wavelength indicates that the compound (1A) causes strong interaction with molecular chains formed by polymerization of the polymerizable liquid crystal compound in the present polarizing film when the compound (1A) is dispersed in the dense molecular chains.

Example 9

The present polarizing film was produced in the same manner as in Example 8, except that the compound (1B) was used in place of the compound (1A). When the local maximum absorption wavelength and the dichroic ratio were measured in the same manner as above, it was found that the local maximum absorption wavelength (λmax1) was 440 nm and the dichroic acid was as high as 28. As described in Example 2, the local maximum absorption wavelength (λmax2) was 398 nm, and therefore it was found that the local maximum absorption wavelength was shifted toward a longer side in wavelength. This result indicates that the compound (1B) causes strong interaction with molecular chains formed by polymerization of the polymerizable liquid crystal compound in the polarizing film when the compound (1B) is dispersed in the dense molecular chains.

Example 10

The present polarizing film was produced in the same manner as in Example 8, except that the compound (4-22)

was used in place of the compound (4-6) and the compound (4-25) was used in place of the compound (4-8), respectively. When the local maximum absorption wavelength and the dichroic ratio were measured in the same manner as above, it was found that the local maximum absorption wavelength (λmax1) was 444 nm and the dichroic acid was as high as 31. As described in Example 1, the local maximum absorption wavelength (λmax2) was 394 nm, and therefore it was found that the local maximum absorption wavelength was shifted toward a longer side in wavelength.

Example 11

The present polarizing film was produced in the same manner as in Example 9, except that the compound (4-22) was used in place of the compound (4-6) and the compound (4-25) was used in place of the compound (4-8), respectively. When the local maximum absorption wavelength and the dichroic ratio were measured in the same manner as above, it was found that the local maximum absorption wavelength (λmax1) was 441 nm and the dichroic acid was as high as 26. As described in Example 2, the local maximum absorption wavelength (λmax2) was 398 nm, and therefore it was found that the local maximum absorption wavelength was shifted toward a longer side in wavelength.

Example 12

The present polarizing film was produced in the same manner as in Example 8, except that the compound (1C) was used in place of the compound (1A). When the local maximum absorption wavelength and the dichroic ratio were measured in the same manner as above, it was found that the local maximum absorption wavelength (λmax1) was 454 nm and the dichroic acid was as high as 21. The local maximum absorption wavelength (λmax2) was 418 nm, and therefore it was found that the local maximum absorption wavelength was shifted toward a longer side in wavelength. This result indicates that the compound (1C) causes strong interaction with molecular chains formed by polymerization of the polymerizable liquid crystal compound in the polarizing film when the compound (1C) was dispersed in the dense molecular chains.

Example 13

The present polarizing film was produced in the same manner as in Example 8, except that the compound (1D) was used in place of the compound (1A). When the local maximum absorption wavelength and the dichroic ratio were measured in the same manner as above, it was found that the local maximum absorption wavelength (λmax1) was 454 nm and the dichroic acid was as high as 23. The local maximum absorption wavelength (λmax2) was 436 nm, and therefore it was found that the local maximum absorption wavelength was shifted toward a longer side in wavelength. This result indicates that the compound (1D) causes strong interaction with molecular chains formed by polymerization of the polymerizable liquid crystal compound in the polarizing film when the compound (1D) was dispersed in the dense molecular chains.

Example 14

The present polarizing film was produced in the same manner as in Example 8, except that the compound (1E) was used in place of the compound (1A). When the local maximum absorption wavelength and the dichroic ratio were measured in the same manner as above, it was found that the local maximum absorption wavelength (λmax1) was 472 nm and the dichroic acid was as high as 36. The local maximum absorption wavelength (λmax2) was 442 nm, and therefore it was found that the local maximum absorption wavelength was shifted toward a longer side in wavelength. This result indicates that the compound (1E) causes strong interaction with molecular chains formed by polymerization of the polymerizable liquid crystal compound in the polarizing film when the compound (1E) was dispersed in the dense molecular chains.

Example 15

The present polarizing film was produced in the same manner as that in Example 8, except that the compound (1F) was used in place of the compound (1A). When the local maximum absorption wavelength and the dichroic ratio were measured in the same manner as above, it was found that the local maximum absorption wavelength (λmax1) was 532 nm and the dichroic acid was as high as 43. The local maximum absorption wavelength (λmax2) was 488 nm, and therefore it was found that the local maximum absorption wavelength was shifted toward a longer side in wavelength. This result indicates that the compound (1F) causes strong interaction with molecular chains formed by polymerization of the polymerizable liquid crystal compound in the polarizing film when the compound (1F) was dispersed in the dense molecular chains.

Example 16

The present polarizing film was produced in the same manner as in Example 8, except that the compound (1G) was used in place of the compound (1A). When the local maximum absorption wavelength and the dichroic ratio were measured in the same manner as above, it was found that the local maximum absorption wavelength (λmax1) was 480 nm and the dichroic acid was as high as 26. The local maximum absorption wavelength (λmax2) was 456 nm, and therefore it was found that the local maximum absorption wavelength was shifted toward a longer side in wavelength. This result indicates that the compound (1G) causes strong interaction with molecular chains formed by polymerization of the polymerizable liquid crystal compound in the polarizing film when the compound (1G) was dispersed in the dense molecular chains.

Example 17

Production of Compound (1) (Compound Represented by the Following Formula (1H) [Compound (1H)])

(1H)

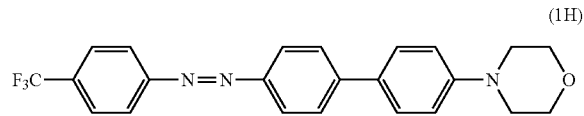

A compound (1H) was synthesized according to the following scheme.

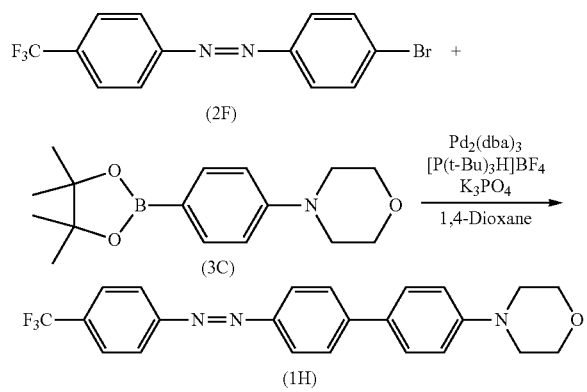

First, 0.25 g of a compound represented by the formula (2F) [compound (2F)], 0.22 g of a compound represented by the formula (3C) [compound (3C)], 0.81 g of potassium phosphate ($K_3PO_4$), 0.0139 g of tris(dibenzylideneacetone) dipalladium(0), 0.0176 g of tri-tert-butylphosphonium tetrafluoroborate, and 5 g of 1,4-dioxane were mixed and stirred at 100° C. for 9 hours under nitrogen atmosphere. The obtained mixed solution was concentrated to remove 1,4-dioxane by distillation, and thereafter refined by silica gel column chromatography (eluent: chloroform and tetrahydrofuran) and concentrated to remove the solvents by distillation. The obtained solid was washed with acetonitrile and thereafter vacuum dried to obtain 0.079 g of a compound (1H), an orange solid. The yield was 25% on the basis of the compound (2F). Spectral data M/Z: 412 (EI-MS), λmax2:391 nm (chloroform solution)

$^1$H-NMR (CDCl$_3$): δ(ppm) 3.24(t, 4H), 3.89(t, 4H), 7.01 (m, 2H), 7.62(m, 2H), 7.74(m, 4H), 8.01(m, 4H).

The compound (2F) was synthesized according to the following scheme.

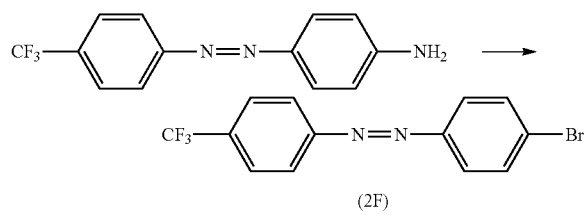

The compound represented by the formula (2F) (hereinafter, referred to as compound (2F)) was synthesized in the same manner as that for the compound (2A), except that 4-trifluoromethyl-4'-aminoazobenzene was used in place of 4-n-butyl-4'-aminoazobenzene in Example 1.

Example 18

Production of Compound (1) (Compound Represented by the Following Formula (1I) [Compound (1I)])

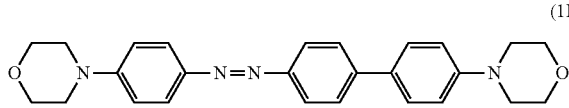

A compound (1I) was synthesized according to the following scheme.

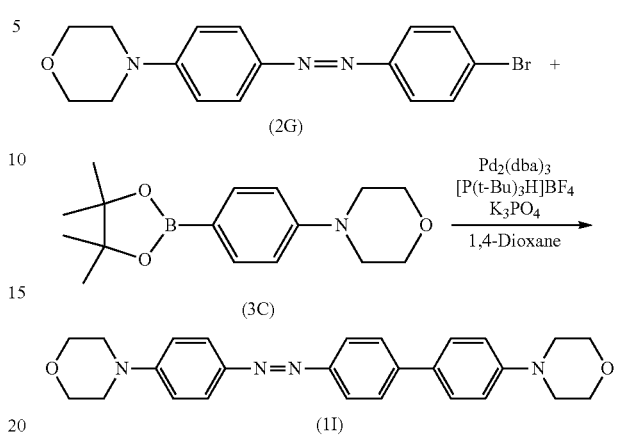

First, 0.25 g of a compound represented by the formula (2G) [compound (2G)], 0.21 g of a compound represented by the formula (3C) [compound (3C)], 0.77 g of potassium phosphate ($K_3PO_4$), 0.0132 g of tris(dibenzylideneacetone) dipalladium(0), 0.0168 g of tri-tert-butylphosphonium tetrafluoroborate, and 5 g of 1,4-dioxane were mixed and stirred at 100° C. for 12 hours under nitrogen atmosphere. The obtained mixed solution was concentrated to remove 1,4-dioxane by distillation, and thereafter refined by silica gel column chromatography (eluent: chloroform and tetrahydrofuran) and concentrated to remove the solvents by distillation. The obtained solid was washed with acetonitrile and thereafter vacuum dried to obtain 0.037 g of a compound (1I), an orange solid. The yield was 12% on the basis of the compound (2G). Spectral data M/Z: 429 (EI-MS), λmax2: 416 nm (chloroform solution).

The compound (2G) was synthesized according to the following scheme.

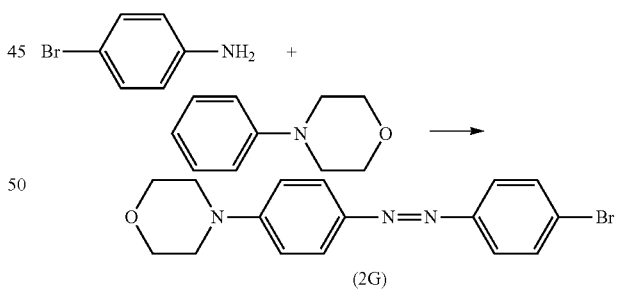

First, 4.0 g of p-bromoaniline, 40 g of water, and 5.2 g of 35% hydrochloric acid were mixed. The mixture was cooled to 0° C. and thereafter 5.3 g of an aqueous 33% sodium nitrite solution was dropwise added. The obtained mixture was stirred for 30 minutes and thereafter 0.23 g of amidosulfuric acid was added. The resulting mixture was dropwise added to a mixture containing 5.7 g of N-phenylmorpholine, 7.6 g of sodium acetate, 114 g of methanol, and 57 g of water at 0° C. A precipitate was collected by filtration and washed with water 3 times. The obtained solid was dried to obtain 5.3 g of the compound (2G), an orange solid.

Example 19

Production of Compound (1) (Compound Represented by the Following Formula (1J) [Compound (1J)])

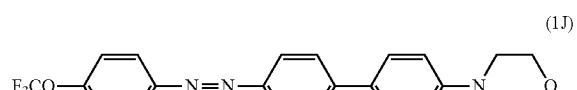
(1J)

A compound (1J) was synthesized according to the following scheme.

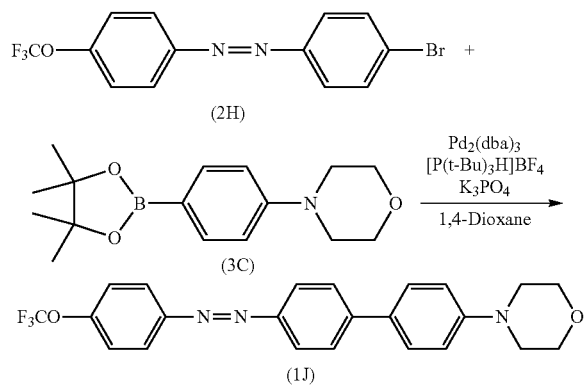

First, 0.30 g of a compound represented by the formula (2H) [compound (2H)], 0.30 g of a compound represented by the formula (3C) [compound (3C)], 0.92 g of potassium phosphate ($K_3PO_4$), 0.0159 g of tris(dibenzylideneacetone)dipalladium(0), 0.0202 g of tri-tert-butylphosphonium tetrafluoroborate, and 6 g of 1,4-dioxane were mixed and stirred at 100° C. for 8 hours under nitrogen atmosphere. The obtained mixed solution was concentrated to remove 1,4-dioxane by distillation, and thereafter refined by silica gel column chromatography (eluent: chloroform and tetrahydrofuran) and concentrated to remove the solvents by distillation. The obtained solid was washed with acetonitrile and thereafter vacuum dried to obtain 0.080 g of a compound (1J), an orange solid. The yield was 22% on the basis of the compound (2H). Spectral data M/Z: 428 (EI-MS), λmax2: 384 nm (chloroform solution)

$^1$H-NMR (CDCl$_3$): δ(ppm) 3.23(t, 4H), 3.88(t, 4H), 7.01 (m, 2H), 7.34(m, 2H), 7.61(m, 2H), 7.72(m, 2H), 7.98(m, 4H).

Example 20

Production of Compound (1) (Compound Represented by the Following Formula (1K) [Compound (1K)])

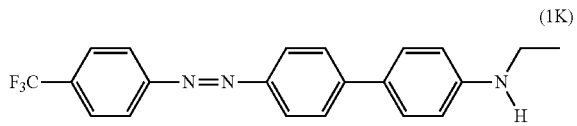 [SMILES: CCNc1ccc(-c2ccc(N=Nc3ccc(C(F)(F)F)cc3)cc2)cc1]
(1K)

A compound (1K) was synthesized according to the following scheme.

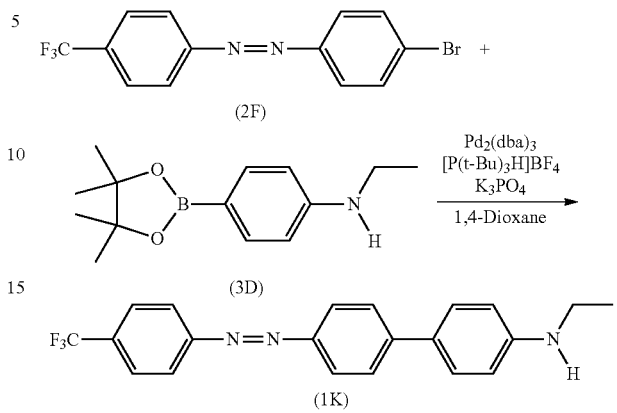

First, 0.50 g of a compound represented by the formula (2F) [compound (2F)], 0.45 g of a compound represented by the formula (3D) [compound (3D)], 1.61 g of potassium phosphate ($K_3PO_4$), 0.0278 g of tris(dibenzylideneacetone)dipalladium(0), 0.0353 g of tri-tert-butylphosphonium tetrafluoroborate, and 10 g of 1,4-dioxane were mixed and stirred at 100° C. for 8 hours under nitrogen atmosphere. The obtained mixed solution was concentrated to remove 1,4-dioxane by distillation, and thereafter refined by silica gel column chromatography (eluent: chloroform and tetrahydrofuran) and concentrated to remove the solvents by distillation. The obtained solid was washed with acetonitrile and thereafter vacuum dried to obtain 0.220 g of a compound (1K), an orange solid. The yield was 39% on the basis of the compound (2F). Spectral data M/Z: 370 (EI-MS), λmax2: 441 nm (chloroform solution)

$^1$H-NMR (CDCl$_3$): δ(ppm) 1.30(t, 3H), 3.23(q, 2H), 6.70 (m, 2H), 7.54(m, 2H), 7.71(m, 4H), 7.98(m, 4H).

Example 21

The present polarizing film was produced in the same manner as in Example 8, except that the compound (1H) was used in place of the compound (1A). When the local maximum absorption wavelength and the dichroic ratio were measured in the same manner as above, it was found that the local maximum absorption wavelength (λmax1) was 432 nm and the dichroic acid was as high as 32. As described in Example 2, the local maximum absorption wavelength (λmax2) was 391 nm, and therefore it was found that the local maximum absorption wavelength was shifted toward a longer side in wavelength. This result indicates that the compound (1H) causes strong interaction with molecular chains formed by polymerization of the polymerizable liquid crystal compound in the polarizing film when the compound (1H) was dispersed in the dense molecular chains.

Example 22

The present polarizing film was produced in the same manner as in Example 8, except the compound (1J) was used in place of the compound (1A). When the local maximum absorption wavelength and the dichroic ratio were measured in the same manner as above, it was found that the local maximum absorption wavelength (λmax1) was 416 nm and the dichroic acid was as high as 33. As described in Example 2, the local maximum absorption wavelength (λmax2) was 384 nm, and therefore it was found that the local maximum absorption wavelength was shifted toward a longer side in wavelength. This result indicates that the compound (1J) causes strong interaction with molecular chains formed by polymerization of the polymerizable liquid crystal compound in the polarizing film when the compound (1J) was dispersed in the dense molecular chains.

Example 23

The present polarizing film was produced in the same manner as in Example 8, except the compound (1K) was used in place of the compound (1A). When the local maximum absorption wavelength and the dichroic ratio were measured in the same manner as above, it was found that the local maximum absorption wavelength (λmax1) was 466 nm and the dichroic acid was as high as 25. As described in Example 2, the local maximum absorption wavelength (λmax2) was 441 nm, and therefore it was found that the local maximum absorption wavelength was shifted toward a longer side in wavelength. This result indicates that the compound (1K) causes strong interaction with molecular chains formed by polymerization of the polymerizable liquid crystal compound in the polarizing film when the compound (1K) was dispersed in the dense molecular chains.

A polarizing film with a high dichroic ratio can be obtained by using the composition of the present invention.

What is claimed is:

1. A composition comprising a compound represented by the formula (1) and a polymerizable liquid crystal compound:

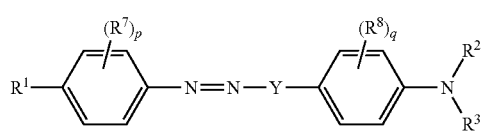

wherein Y represents a group represented by the formula (Y1) or the formula (Y2);
$R^1$ represents an alkyl group having 1 to 20 carbon atoms, an alkoxy group having 1 to 20 carbon atoms, or —N(R)(R⁰); wherein R and $R^0$ each independently represent a hydrogen atom or an alkyl group having 1 to 10 carbon atoms, or R and $R^0$ are bonded together to form a ring together with the nitrogen atom to which R and $R^0$ are bonded; one or more hydrogen atoms constituting the alkyl group having 1 to 20 carbon atoms, the alkoxy group having 1 to 20 carbon atoms, or the alkyl group having 1 to 10 carbon atoms are independently optionally substituted with an atom or a group selected from the group consisting of a halogen atom, a hydroxyl group and an optionally substituted amino group; the alkyl group having 1 to 20 carbon atoms, the alkoxy group having 1 to 20 carbon atoms, and the alkyl group having 1 to 10 carbon atoms each optionally have an ether linkage (—O—) between carbon atoms constituting them;
$R^7$ and $R^8$ are substituents other than a hydrogen atom and are each independently an alkyl group having 1 to 4 carbon atoms, an alkoxy group having 1 to 4 carbon atoms, a halogen atom, or a cyano group; one or more hydrogen atoms constituting the alkyl group having 1 to 4 carbon atoms or the alkoxy group having 1 to 4 carbon atoms are independently optionally substituted with a halogen atom or a hydroxyl group; p and q are each independently an integer of 0 to 2;
$R^2$ and $R^3$ each independently represent a hydrogen atom or an alkyl group having 1 to 10 carbon atoms, or $R^2$ and $R^3$ are bonded together to form a ring together with the nitrogen atom to which $R^2$ and $R^3$ are bonded; one or more hydrogen atoms constituting the alkyl group having 1 to 10 carbon atoms are independently optionally substituted with an atom or a group selected from the group consisting of a halogen atom, a hydroxyl group and an optionally substituted amino group; and the alkyl group having 1 to 10 carbon atoms optionally have an ether linkage (—O—) between carbon atoms constituting it;

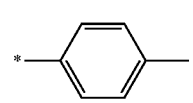

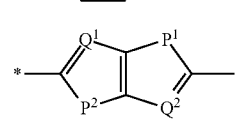

wherein * shows a bonding site to N;
$P^1$ and $P^2$ each independently represent a sulfur atom, an oxygen atom or —NR¹⁰— wherein $R^{10}$ represents a hydrogen atom or an alkyl group having 1 to 4 carbon atoms;
$Q^1$ and $Q^2$ each independently represent a nitrogen atom or =CH—.

2. The composition according to claim 1, wherein the compound represented by the formula (1) is a compound represented by the formula (1a):

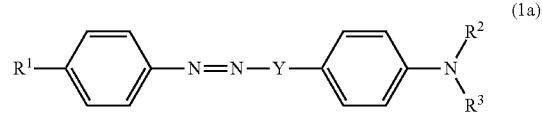

wherein Y and $R^1$ to $R^3$ respectively represent as defined in claim 1.

3. The composition according to claim 1, wherein the polymerizable liquid crystal compound exhibits a smectic liquid crystal phase.

4. The composition according to claim 1, wherein the composition further comprises a polymerization initiator.

5. A polarizing film formed from the composition according to claim 1.

6. The polarizing film according to claim 5, wherein a local maximum absorption wavelength (λmax1) of the polarizing film according to claim 5 is longer than a local maximum absorption wavelength (λmax2) of the compound represented by the formula (1) contained in the polarizing film.

7. The polarizing film according to claim 6, wherein a difference between λmax 1 and λmax 2 is 15 nm or longer.

8. The polarizing film according to claim 5, wherein the polarizing film exhibits a Bragg peak in x-diffraction measurement.

9. A liquid crystal display device comprising the polarizing film according to claim 5.

10. A liquid crystal cell comprising a substrate, a liquid crystal layer, and the polarizing film according to claim 5.

11. The liquid crystal cell according to claim 10, wherein the polarizing film is disposed between the substrate and the liquid crystal layer.

12. The liquid crystal cell according to claim 11, further comprising a color filter disposed between the substrate and the liquid crystal layer.

13. A circularly polarizing plate comprising the polarizing film according to claim 5 and a ¼ wavelength plate.

14. An organic EL display device comprising the circularly polarizing plate according to claim 13 and an organic EL element.

* * * * *